(12) United States Patent
Sharma et al.

(10) Patent No.: US 12,082,926 B2
(45) Date of Patent: Sep. 10, 2024

(54) OPTICAL SENSOR WITH MULTIPLE DETECTORS OR MULTIPLE EMITTERS

(71) Applicant: Masimo Corporation, Irvine, CA (US)

(72) Inventors: Vikrant Sharma, Santa Ana, CA (US); Mohammad Usman, Mission Viejo, CA (US)

(73) Assignee: Masimo Corporation, Irvine, CA (US)

( * ) Notice: Subject to any disclaimer, the term of this patent is extended or adjusted under 35 U.S.C. 154(b) by 516 days.

(21) Appl. No.: 17/379,756

(22) Filed: Jul. 19, 2021

(65) Prior Publication Data
US 2022/0039707 A1  Feb. 10, 2022

Related U.S. Application Data

(60) Provisional application No. 63/135,933, filed on Jan. 11, 2021, provisional application No. 63/060,868, filed on Aug. 4, 2020.

(51) Int. Cl.
| | |
|---|---|
| A61B 5/1455 | (2006.01) |
| A61B 5/00 | (2006.01) |
| A61B 5/024 | (2006.01) |
| A61B 5/145 | (2006.01) |

(52) U.S. Cl.
CPC ........ *A61B 5/14551* (2013.01); *A61B 5/0004* (2013.01); *A61B 5/024* (2013.01); *A61B 5/14532* (2013.01); *A61B 5/6824* (2013.01); *A61B 5/6826* (2013.01)

(58) Field of Classification Search
CPC ..... A61B 5/0205; A61B 5/024; A61B 5/1455; A61B 5/14551; A61B 5/14552; A61B 5/6824; A61B 5/6826; A61B 5/02438; A61B 5/6802; A61B 5/14532
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,209,230 A | * 5/1993 | Swedlow | ........... A61B 5/02427 356/41 |
| 5,319,355 A | 6/1994 | Russek | |

(Continued)

OTHER PUBLICATIONS

US 2024/0016391 A1, 01/2024, Lapotko et al. (withdrawn)

*Primary Examiner* — Chu Chuan Liu
(74) *Attorney, Agent, or Firm* — Knobbe, Martens, Olson & Bear, LLP

(57) ABSTRACT

Various noninvasive physiological sensors are described herein. Some implementations of the sensors described herein include multiple emitters and/or detectors positioned at various portions of a measurement site and configured to operate in either or both of transmittance and reflectance modes. In one implementation, a noninvasive physiological sensor includes a body portion configured to secure to a finger of a subject, an emitter operably positioned by the body portion at a first side of the finger and configured to emit light of one or more wavelengths into tissue of the finger, a first detector operably positioned by the body portion at a second side of the finger opposite the first side, and a second detector operably positioned by the body portion at a third side of the finger and offset approximately 90 degrees from the emitter with respect to an axis extending through at least a portion of the body portion.

20 Claims, 14 Drawing Sheets

(56) References Cited

U.S. PATENT DOCUMENTS

| | | | |
|---|---|---|---|
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,766,131 A * | 6/1998 | Kondo ............ A61B 5/681 600/502 |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 5,999,834 A * | 12/1999 | Wang ............ A61B 5/6833 600/344 |
| 6,002,952 A | 12/1999 | Diab et al. |
| 6,010,937 A | 1/2000 | Karam et al. |
| 6,014,576 A * | 1/2000 | Raley ............ A61B 5/6833 600/344 |
| 6,018,673 A | 1/2000 | Chin et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |

(56) References Cited

U.S. PATENT DOCUMENTS

| | | |
|---|---|---|
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,311,601 B2 | 11/2012 | Besko |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,818,476 B2 | 8/2014 | Besko |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Ai-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |

(56) References Cited

U.S. PATENT DOCUMENTS

| | | |
|---|---|---|
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Ai-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Ai-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Ai-Ali |
| RE49,034 E | 4/2022 | Ai-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |

(56) References Cited

U.S. PATENT DOCUMENTS

| | | |
|---|---|---|
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| 11,951,186 B2 | 4/2024 | Krishnamani et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0122520 A1* | 6/2006 | Banet ................ A61B 5/6814 600/323 |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099962 A1* | 4/2010 | Chung ................ A61B 5/6826 600/323 |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0119266 A1* | 5/2017 | Wong ................ A61B 5/6817 |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0310823 A1 | 11/2018 | Al-Ali et al. |
| 2019/0117070 A1 | 4/2019 | Muhsin et al. |
| 2019/0239787 A1 | 8/2019 | Pauley et al. |
| 2019/0320906 A1 | 10/2019 | Olsen |
| 2019/0374713 A1 | 12/2019 | Kiani et al. |
| 2020/0037453 A1 | 1/2020 | Triman et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |

(56) References Cited

U.S. PATENT DOCUMENTS

| | | |
|---|---|---|
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |

\* cited by examiner

OPTICAL SENSOR WITH MULTIPLE DETECTORS OR MULTIPLE EMITTERS

INCORPORATION BY REFERENCE TO ANY PRIORITY APPLICATIONS

This application claims the benefit of priority under 35 U.S.C. § 119(e) to U.S. Patent Application No. 63/135,933, entitled "OPTICAL SENSOR WITH MULTIPLE DETECTORS OR MULTIPLE EMITTERS," filed Jan. 11, 2021 and U.S. Patent Application No. 63/060,868, entitled "OPTICAL SENSOR WITH MULTIPLE DETECTORS OR MULTIPLE EMITTERS," filed Aug. 4, 2020. All of the above-mentioned applications are incorporated by reference herein in their entireties. Any and all applications for which a foreign or domestic priority claim is identified in the Application Data Sheet as filed with the present application are hereby incorporated by reference under 37 CFR 1.57.

TECHNICAL FIELD

The present disclosure relates to devices, methods, and systems for monitoring a subject's physiological information. More specifically, the present disclosure relates to noninvasive measurement of the physiological information using multiple sources of data derived from an optical sensor.

BACKGROUND

Hospitals, nursing homes, and other patient care facilities typically include patient monitoring devices in the facility. Patient monitoring devices can include sensors, processing equipment, and displays for obtaining and analyzing a medical patient's physiological parameters such as blood oxygen saturation level, respiratory rate, pulse, and a myriad of other parameters, such as those monitored on commercially available patient monitors from Masimo Corporation of Irvine, California. Clinicians, including doctors, nurses, and other medical personnel, use the physiological parameters and trends of those parameters obtained from patient monitors to diagnose illnesses and to prescribe treatments. Clinicians also use the physiological parameters to monitor patients during various clinical situations to determine whether to adjust the level of medical care given to patients.

Patient monitoring can be achieved through spectroscopic analysis using, for example, a pulse oximeter. A pulse oximeter generally includes one or more light sources transmitting optical radiation into or reflecting off through a portion of the body, for example a finger, a hand, a foot, a nose, an earlobe, or a forehead. One or more photo detection devices detect the light after interaction with tissue of the portion of the body, and output one or more detector signals responsive to the detected attenuated light. One or more signal processing devices process the detector signals and output a measurement indicative of a physiological parameter or characteristic, such as oxygen saturation ($SpO_2$), pulse rate, a plethysmograph waveform, perfusion index (PI), pleth variability index (PVI), methemoglobin (MetHb), carboxyhemoglobin (CoHb), total hemoglobin (tHb), blood glucose, etc., and a display may display any one or any combination of the foregoing parameters individually, in groups, in trends, as combinations, or as an overall wellness or other index. An example of such an oximeter is described in U.S. Pat. No. 9,323,176, filed May 27, 1999, entitled "Stereo Pulse Oximeter," now U.S. Pat. No. 6,334,065, the disclosure of which is hereby incorporated by reference in its entirety.

SUMMARY

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

Disclosed herein are devices (also referred to herein as "sensors") that can include multiple detectors and/or multiple emitters that are arranged and/or spatially configured such that the devices can obtain measurements that relate to different path lengths or different tissue geometries. Such configurations can improve determinations of physiological parameters with respect to accuracy, reliability, or robustness, for example by reducing the likelihood of a total measurement error. Any of the devices described herein can be secured to various portions of a subject's body. For example, any of the devices described herein can be secured to a digit of the subject, such as a finger, a toe, or another portion of the subject's body, such as an ear, nose, arm, wrist, among others. Accordingly, although some implementations of the present disclosure describe devices configured to secure to a finger of a user, the present disclosure is not so limited. Any of the devices described herein can be configured to interact with other devices via mechanical and/or electrical connection and/or via wired and/or wireless communication methods. Any of the devices described herein can be configured to determine one or more physiological parameters of a subject based on, for example, signals generated from one or more sensors (for example, an optical sensor) of the device, and/or any of the devices described herein can be configured to communicate with a separate device to facilitate determination of such one or more physiological parameters by such separate device. Any of the devices described herein can be utilized for noninvasive determination of one or more physiological parameters.

Disclosed herein is a noninvasive physiological sensor configured to attach to a finger of a user, the noninvasive physiological sensor comprising: a body portion configured to be secured to the finger of the user; a first emitter configured to emit light of one or more wavelengths into tissue of the finger of the user when the noninvasive physiological sensor is in use, wherein the first emitter is operably positioned by the body portion at a first side of the finger when the body portion is secured to the finger; and a plurality of detectors, each of the plurality of detectors configured to detect at least a portion of the emitted light after attenuation by the tissue of the finger of the user when the noninvasive physiological sensor is in use, wherein each of the plurality of detectors is configured to generate at least one signal responsive to the detected light, and wherein the plurality of detectors comprises: a first detector operably positioned by the body portion at a second side of the finger that is opposite the first side of the finger when the body portion is secured to the finger such that the first detector and the first emitter are substantially aligned with one another; and a second detector operably positioned by the body portion at a third side of the finger when the body portion is secured to the finger such that the second detector is offset approximately 90 degrees from the first emitter with respect to an axis extending through at least a portion of the body portion.

In some implementations: the noninvasive physiological sensor further comprises a second emitter configured to emit light of one or more wavelengths into the tissue of the finger of the user when the noninvasive physiological sensor is in use; and the second emitter is operably positioned by the body portion at a fourth side of the finger that is opposite the third side of the finger when the body portion is secured to the finger such that the second emitter is offset approximately 90 degrees from the first emitter with respect to said axis extending through at least the portion of the body portion. In some implementations, the second emitter is operably positioned by the body portion such that the second emitter is offset approximately 180 degrees from the second detector with respect to said axis extending through at least the portion of the body portion. In some implementations, the first emitter and the second emitter are configured to be selectively activated such that only one of the first and second emitters is emitting light at a given time.

In some implementations, said axis extends through a center of a cross-section of the body portion. In some implementations, the first emitter and the plurality of detectors are operably positioned by the body portion along a plane of a cross-section of the body portion when secured to the finger of the user. In some implementations, said body portion is configured such that, when secured to the finger of the user, said axis extends along at least a portion of a longitudinal axis of the finger. In some implementations, said first emitter is the only emitter of the noninvasive physiological sensor.

In some implementations, the body portion is configured to be transitioned from a first configuration when not secured to the finger of the user to a second configuration when secured to the finger of the user, and wherein the first and second configurations are different. In some implementations, the body portion is configured to be substantially flat when in the first configuration. In some implementations, the body portion is configured such that, when in the second configuration, the body portion is wrapped around the finger of the user. In some implementations, when the body portion is in said second configuration, a cross-section of the body portion is rounded.

In some implementations, in the plurality of detectors further comprises a third detector operably positioned by the body portion at a fourth side of the finger when the body portion is secured to the finger such that the third detector is offset approximately 90 degrees from the first emitter with respect to said axis extending through said at least the portion of the body portion. In some implementations, the third detector is operably positioned by the body portion at the fourth side of the finger when the body portion is secured to the finger such that the third detector is offset approximately 180 degrees from the second detector with respect to said axis extending through at least the portion of the body portion.

In some implementations, the first emitter and the plurality of detectors are in communication with a monitoring device configured to: control operation of the first emitter; receive said at least one signal generated by each of the plurality of detectors; and determine one or more physiological parameters based on said at least one signal generated by each of the plurality of detectors. In some implementations, the one or more physiological parameters comprises at least one of oxygen saturation, pulse rate, and glucose. In some implementations, the noninvasive physiological sensor further comprises a cable connected to the body portion and configured to transmit said at least one signal generated by each of the plurality of detectors to said monitoring device. In some implementations, said monitoring device is configured to attach to a wrist of the user. In some implementations, said monitoring device is configured to wirelessly transmit said determined one or more physiological parameters. In some implementations, said noninvasive physiological sensor is configured to wirelessly transmit said at least one signal from each of the plurality of detectors to said monitoring device.

In some implementations, said noninvasive physiological sensor is configured to determine one or more physiological parameters based on said at least one signal generated by each of the plurality of detectors. In some implementations, the first side of the finger comprises a nail-bed of the finger.

Disclosed herein is a noninvasive physiological sensor configured to attach to a finger of a user, the noninvasive physiological sensor comprising: a body portion configured to be secured to the finger of the user; a first emitter configured to emit light of one or more wavelengths into tissue of the finger of the user when the noninvasive physiological sensor is in use, wherein the first emitter is operably positioned by the body portion at a first side of the finger when the body portion is secured to the finger; a second emitter configured to emit light of one or more wavelengths into the tissue of the finger of the user when the noninvasive physiological sensor is in use, wherein the second emitter is operably positioned by the body portion at a second side of the finger that is opposite the first side of the finger when the body portion is secured to the finger; and a plurality of detectors, each of the plurality of detectors configured to detect at least a portion of the emitted light after attenuation by the tissue of the finger of the user when the noninvasive physiological sensor is in use, wherein each of the plurality of detectors is configured to generate at least one signal responsive to the detected light, and wherein the plurality of detectors comprises: a first detector operably positioned by the body portion at the second side of the finger when the body portion is secured to the finger such that the first detector is spaced from the second emitter by a first distance, wherein the first detector and the first emitter are configured to operate in a first transmissive mode and wherein the first detector and the second emitter are configured to operate in a first reflectance mode; and a second detector operably positioned by the body portion at the second side of the finger when the body portion is secured to the finger such that the second detector is spaced from the second emitter by a second distance that is greater than the first distance, wherein the second detector and the first emitter are configured to operate in a second transmissive mode and wherein the second detector and the second emitter are configured to operate in a second reflectance mode.

In some implementations, the body portion is configured to be transitioned from a first configuration when not secured to the finger of the user to a second configuration when secured to the finger of the user, and wherein the first and second configurations are different. In some implementations, when the body portion is in the first configuration, the first detector, the second detector, and the second emitter are aligned with one another. In some implementations, the body portion is configured to be substantially flat when in the first configuration. In some implementations, the body portion is configured such that, when in the second configuration, the body portion is wrapped around the finger of the user. In some implementations, when the body portion is in the second configuration, a cross-section of the body portion is rounded.

In some implementations, said first and second reflectance modes are configured to operate simultaneously. In some implementations, only one of said first and second reflectance modes are configured to operate at a given time. In some implementations, said first and second transmissive modes are configured to operate simultaneously. In some implementations, only one of said first and second transmissive modes are configured to operate at a given time. In some implementations, the first and second reflective modes are configured to operate simultaneously with one another and with the first and second transmissive modes.

In some implementations, the first side of the finger comprises a nail-bed of the finger. In some implementations, the second emitter and the plurality of detectors are operably positioned by the body portion along a plane that is substantially parallel to at least one of a first axis extending through at least a portion of the body portion when secured to the finger and a second axis extending along at least a portion of the finger when the body portion is secured to the finger. In some implementations: at least a portion of the light emitted by the first emitter is transmitted through the tissue of the finger and detected by the first detector and the second detector; and at least a portion of the light emitted by the second emitter is reflected by the tissue of the finger and detected by the first detector and the second detector.

In some implementations, the first and second emitters and the plurality of detectors are in communication with a monitoring device configured to: control operation of the first and second emitters; receive said at least one signal generated by each of the plurality of detectors; and determine one or more physiological parameters based on said at least one signal generated by each of the plurality of detectors. In some implementations, one or more physiological parameters comprises at least one of oxygen saturation, pulse rate, and glucose. In some implementations, the noninvasive physiological sensor further comprises a cable connected to the body portion and configured to transmit said at least one signal generated by each of the plurality of detectors to said monitoring device. In some implementations, said monitoring device is configured to attach to a wrist of the user. In some implementations, said monitoring device is configured to wirelessly transmit said determined one or more physiological parameters. In some implementations, said noninvasive physiological sensor is configured to wirelessly transmit said at least one signal from each of the plurality of detectors to said monitoring device.

Disclosed herein is a noninvasive physiological sensor configured to attach to a finger of a user, the noninvasive physiological sensor comprising: a body portion configured to be secured to the finger of the user; a first emitter configured to emit light of one or more wavelengths into tissue of the finger of the user when the noninvasive physiological sensor is in use, wherein the first emitter is operably positioned by the body portion at a first side of the finger when the body portion is secured to the finger; and a plurality of detectors, each of the plurality of detectors configured to detect at least a portion of the emitted light after attenuation by the tissue of the finger of the user when the noninvasive physiological sensor is in use, wherein each of the plurality of detectors is configured to generate at least one signal responsive to the detected light, and wherein the plurality of detectors comprises: a first detector operably positioned by the body portion at a second side of the finger that is opposite the first side of the finger when the body portion is secured to the finger such that the first detector is offset approximately 180 degrees from the first emitter with respect to an axis extending through at least the portion of the body portion; and a second detector operably positioned by the body portion at the second side of the finger when the body portion is secured to the finger such that the second detector is aligned with but spaced from the first detector by a first distance.

In some implementations, the first and second detectors are configured to concurrently operate in a transmissive mode with the first emitter. In some implementations, said first emitter is the only emitter of the noninvasive physiological sensor. In some implementations, the body portion does not operably position any emitters at the second side of the finger when the body portion is secured to the finger. In some implementations: the plurality of detectors comprises a third detector operably positioned by the body portion at the second side of the finger when the body portion is secured to the finger such that the third detector is aligned with but spaced from the first detector by a second distance and aligned with but spaced from the second detector by a third distance that is greater than the second distance. In some implementations, the first, second, and third detectors are configured to concurrently operate in said transmissive mode with the first emitter. In some implementations, said first and second distances are equal.

In some implementations, the body portion is configured to be transitioned from a first configuration when not secured to the finger of the user to a second configuration when secured to the finger of the user, and wherein the first and second configurations are different. In some implementations, when the body portion is in the first configuration, the first detector, the second detector, and the first emitter are aligned with one another. In some implementations, the body portion is configured to be substantially flat when in the first configuration. In some implementations, the body portion is configured such that, when in the second configuration, the body portion is wrapped around the finger of the user. In some implementations, when the body portion is in the second configuration, a cross-section of the body portion is rounded.

In some implementations, the first emitter and the plurality of detectors are in communication with a monitoring device configured to: control operation of the first emitter; receive said at least one signal generated by each of the plurality of detectors; and determine one or more physiological parameters based on said at least one signal generated by each of the plurality of detectors. In some implementations, the one or more physiological parameters comprises at least one of oxygen saturation, pulse rate, and glucose. In some implementations, the noninvasive physiological sensor further comprises a cable connected to the body portion and configured to transmit said at least one signal generated by each of the plurality of detectors to said monitoring device. In some implementations, said monitoring device is configured to attach to a wrist of the user. In some implementations, said monitoring device is configured to wirelessly transmit said determined one of more physiological parameters. In some implementations, said noninvasive physiological sensor is configured to wirelessly transmit said at least one signal from each of the plurality of detectors to said monitoring device. In some implementations, said noninvasive physiological sensor is configured to determine one or more physiological parameters based on said at least one signal generated by each of the plurality of detectors. In some implementations, the first side of the finger comprises a nail-bed of the finger.

Disclosed herein is a noninvasive physiological sensor configured to attach to a finger of a patient, the sensor comprising: a first emitter configured to emit light and configured to be positioned on or around a nail-bed of the finger when the sensor is in use; and a plurality of detectors, wherein each of the plurality of detectors is configured to detect at least some of the light after attenuation by tissue of the patient and generate at least one signal responsive to the detected light. The plurality of detectors can comprise: a first detector configured to be positioned opposite the first emitter relative to the finger when the sensor is in use, and a second detector configured to be positioned on a side of the finger when the sensor is in use such that the second detector is offset about 90 degrees from the first emitter with respect to a longitudinal axis of the finger.

The plurality of detectors can further comprise a third detector configured to be positioned opposite the second detector relative to the finger when the sensor is in use such that the third detector is offset about 90 degrees from the first emitter with respect to the longitudinal axis of the finger. The sensor can further comprise a second emitter configured to be positioned opposite the second detector relative to the finger when the sensor is in use such that the second emitter is offset about 90 degrees from the first emitter with respect to the longitudinal axis of the finger. The first emitter and the second emitter can be selectively activated so that only one of the first emitter or the second emitter is emitting light at a given time. In some variants, said about 90 degrees is between 80 and 100 degrees, between 87 and 93 degrees, between 89 and 91 degrees, or exactly 90 degrees.

In some variants, the first emitter is activated for a first quarter cycle, the second emitter is activated for a third quarter cycle, and the first emitter and the second emitter are off for a second quarter cycle and a fourth quarter cycle. In some variants, a particular path length of the light detected by a particular one of the plurality of detectors is different from a path length of the light detected by all other ones of the plurality of detectors. When the sensor is attached to the patient, the emitter and the plurality of detectors can be configured to be located on a same 2D plane. When the sensor is attached to the finger of the patient, the first emitter, the second emitter, and the plurality of detectors can be located on a same 2D plane. The plurality of detectors can be communicatively coupled to a patient monitor and the patient monitor can be configured to: receive the signals generated by the plurality of detectors; and determine a physiological parameter based at least in part on at least one of the received signals. In some variants, the patient monitor receives the signals as a time-division-multiplexed signal. The physiological parameter can comprise at least one of total hemoglobin, oxygen saturation, pulse rate, a plethysmograph waveform, perfusion index, pleth variability index, methemoglobin, carboxyhemoglobin, or glucose. The sensor can comprise a wearable apparatus, a fingertip sleeve configured to couple to the finger, tape for securing the sensor to the finger, an L-shaped sensor, and/or a tape sensor. In some variants, none of the plurality of detectors are positioned on a knuckle of the patient when the sensor is in use.

Disclosed herein is a noninvasive physiological sensor comprising: an emitter configured to emit light; a detector configured to detect the light after attenuation by tissue of a patient and generate at least one signal corresponding to the detected light; and a motorized component configured to move the emitter along a longitudinal axis of a finger of the patient when the sensor is in use, wherein, responsive to receiving a first command signal, the motorized component moves the emitter from a first position on a nail-side of the finger to a second position off the nail-side of the finger. The detector can be configured to be positioned opposite the emitter relative to the finger when the sensor is in use. The detector can be configured to be positioned on a side of the finger when the sensor is in use such that the detector is offset 90 degrees from the emitter with respect to the longitudinal axis of the finger. In some variants, the emitter moves relative to the detector. The motorized component can be further configured to move the detector along the longitudinal axis of the finger when the sensor is in use, and the motorized component can be configured to receive a second command signal from a controller, wherein, responsive to receiving said second command signal, the motorized component moves the detector along the longitudinal axis of the finger. Responsive to receiving a second command signal, the motorized component can move the emitter from the second position to the first position. Responsive to receiving a third command signal, the motorized component can move the emitter from the second position to a third position, wherein the third position is different from the first position.

The emitter can be configured to emit light at each of the first position and the second position. In some variants, a path length of the light detected by the detector when the emitter is at the first position is different from a path length of the light detected by the detector when the emitter is at the second position. The detector can be communicatively coupled to a patient monitor and the patient monitor can be configured to: receive the at least one signal generated by the detector; and determine a physiological parameter based at least in part on the received at least one signal. The physiological parameter can comprise at least one of total hemoglobin, oxygen saturation, pulse rate, a plethysmograph waveform, perfusion index, pleth variability index, methemoglobin, carboxyhemoglobin, or glucose. The sensor can comprise a wearable apparatus, a fingertip sleeve configured to couple to the finger, tape for securing the sensor to the finger, an L-shaped sensor, and/or a tape sensor. In some variants, none of the plurality of detectors are positioned on a knuckle of the patient when the sensor is in use.

Disclosed herein is a noninvasive physiological sensor configured to attach to a finger of a user, the sensor comprising: a first emitter configured to emit light and configured to be positioned on or around a first side of the finger when the sensor is in use; a second emitter configured to emit light and configured to be positioned on or around a second side of the finger when the sensor is in use; and a plurality of detectors, wherein each of the plurality of detectors is configured to detect at least some of the light emitted by the first and second emitters after attenuation by tissue of the finger, each of the plurality of detectors further configured to generate at least one signal responsive to the detected light. The plurality of detectors can comprise: a first detector configured to be positioned on the second side of the finger when the sensor is in use; and a second detector configured to be positioned on the second side of the finger and adjacent to the first detector when the sensor is in use.

The first side of the finger can comprise a nail-bed of the finger. The second side of the finger can be opposite the first side of the finger. The first side can be a top portion of the finger and the second side can be a bottom portion of the finger. The first detector, the second detector, and the second emitter can be aligned along a plane with one another when the sensor is in use, said plane being parallel to a longitudinal axis of the finger. The first emitter and the first detector or the second detector can be aligned along a plane that is orthogonal to a longitudinal axis of the finger. The light emitted by the first emitter can be transmitted through the tissue of the finger and detected by the first detector and the second detector, and the light emitted by the second emitter can be reflected by the tissue of the finger and detected by the first detector and the second detector. The generated signals can be associated with transmittance and reflectance of the light emitted by the first emitter and the second emitter. In some variants, the first detector is offset from the first emitter by a first degree amount with respect to a longitudinal axis of the finger, and the second detector is offset from the first emitter by a second degree amount with respect to a longitudinal axis of the finger. The first emitter and the second emitter can be selectively activated so that only one of the first emitter or the second emitter is emitting light at a given time.

In some variants, the first emitter is activated for a first quarter cycle, the second emitter is activated for a third quarter cycle, and the first emitter and the second emitter are off for a second quarter cycle and a fourth quarter cycle. In some variants, a particular path length of the light detected by a particular one of the plurality of detectors is different from a path length of the light detected by all other ones of the plurality of detectors. The plurality of detectors can be communicatively coupled to a patient monitor and the patient monitor can be configured to: receive the signals generated by the plurality of detectors; and determine a physiological parameter based at least in part on at least one of the received signals. In some variants, the patient monitor receives the signals as a time-division-multiplexed signal. The physiological parameter can comprise at least one of total hemoglobin, oxygen saturation, pulse rate, a plethysmograph waveform, perfusion index, pleth variability index, methemoglobin, carboxyhemoglobin, or glucose. The sensor can comprise a wearable apparatus, a fingertip sleeve configured to couple to the finger, tape for securing the sensor to the finger, an L-shaped sensor, and/or a tape sensor. In some variants, none of the plurality of detectors are positioned on a knuckle of the patient when the sensor is in use.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

DETAILED DESCRIPTION

Although certain embodiments and examples are described below, those of skill in the art will appreciate that the disclosure extends beyond the specifically disclosed embodiments or uses and obvious modifications and equivalents thereof. Thus, it is intended that the scope of the disclosure herein disclosed should not be limited by any particular embodiments described below.

There are many sources of potential measurement error introduced to pulse oximetry systems. Some such sources of error include the pulse oximetry system's electronic components, including emitters and detectors, as well as chemical and structural physiological differences between patients. Another source of measurement error is the particular tissue geometry of a measurement site.

To address these or other problems, a sensor can include multiple emitters or multiple detectors that are arranged and/or spatially configured such that the sensor can generate signals that relate to different path lengths and/or different tissue geometries. In this way, the sensor can reduce the likelihood of a measurement error caused by a particular tissue geometry, thereby improving the accuracy, reliability, and/or robustness of the sensor. Additionally or alternatively, the sensor can include improved accuracy, reliability, or robustness by using any of various arbitration techniques to select or to combine estimations from the various signals (for example, generated by any one of a plurality of detectors of a sensor), or to determine a confidence parameter.

System Overview

Figure 1A:
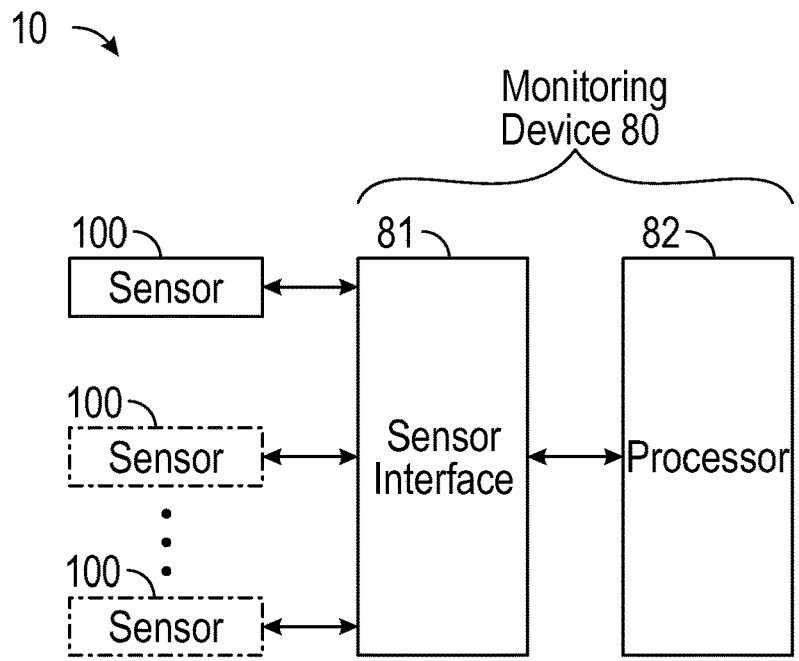
FIG. 1A illustrates a block diagram of a monitoring system in accordance with aspects of this disclosure.

FIG. 1A shows an illustrative monitoring system 10 that can be utilized to determine one or more physiological parameters of a subject. As shown, system 10 can include a monitoring device 80 and a sensor 100, which can be configured to communicate with one another. In some implementations, monitoring device 80 and sensor 100 are configured to be mechanically and/or electrically connected to one another. In some implementations, monitoring device 80 and sensor 100 are not mechanically and/or electrically connected to one another, but rather, are configured to communicate with one another wirelessly. In some implementations, the sensor 100 can generate sensor data relating to a physiological parameter associated with a subject (e.g., a patient). For example, the sensor 100 can include one or more detectors which can generate one or more signals responsive to light attenuated by tissue of the subject that is emitted by one or more emitters of the sensor 100. The monitoring device 80 can obtain such sensor data from the sensor 100 and can determine one or more physiological parameters based on the sensor data. System 10 can include any number of sensor(s) 100, such as one, two, three, four, five, or six or more sensors 100, as shown in FIG. 1A.

The monitoring device 80 can include a sensor interface 81 and a processor 82. The sensor 100 can provide a stream of data to the monitoring device 80. For example, the sensor 100 can provide a stream of data to the sensor interface 81 and/or to the processor 82 (for example, via the sensor interface 81). The sensor 100 can be connected to the sensor interface 81 via a wired or wireless connection. An output of the sensor interface 81 can be fed into the processor 82 in a raw or partially processed data form. Partially processed sensor data can be demodulated, filtered, or otherwise processed to prepare the data for use by the processor 82 to calculate measurements of one or more physiological parameters. Partially processing the sensor data can include generating basic ratios of wavelengths in a multi-wavelength system. The processor 82 can include one or more hardware or software signal processors. Partial processing can include, for example, a low or high pass filter or other preprocessing steps typically performed in a signal acquisition system.

The unprocessed or partially processed streams of data from the sensor 100 can be combined by the processor 82 into combined sensor data. The combined sensor data can include a plurality of features of the signals from the sensor 100, such as amplitude, phase, AC value, DC value, or others. Measurement site or body tissue information can be provided to the processor 82 as independent features. The processor 82 can produce one or more measurements of a physiological parameter based on the combined sensor data. The plurality of features of the signals can be mapped onto empirical data, which can provide estimates of physiological parameter measurements. The additional independent features of the measurement site or body tissue information can provide more combinations of features and improve the estimation of the physiological parameters. The combinations of features can be linear or can include high-ordered combinations. The processor 82 can analyze from the combined sensor data various features, such as a ratiometric value, such as ratios of attenuated light of one wavelength to attenuated light of another wavelength, or combinations of features, including non-normalized features, data from bulk absorption or peripheral absorption signals, or others. The sensor 100 and monitoring device 80 can be utilized to obtain a physiological parameter or characteristic, such as oxygen saturation ($SpO_2$), pulse rate, a plethysmograph waveform, perfusion index (PI), pleth variability index (PVI), methemoglobin (MetHb), carboxyhemoglobin (CoHb), total hemoglobin (tHb), blood glucose, among other things.

Figure 1B:
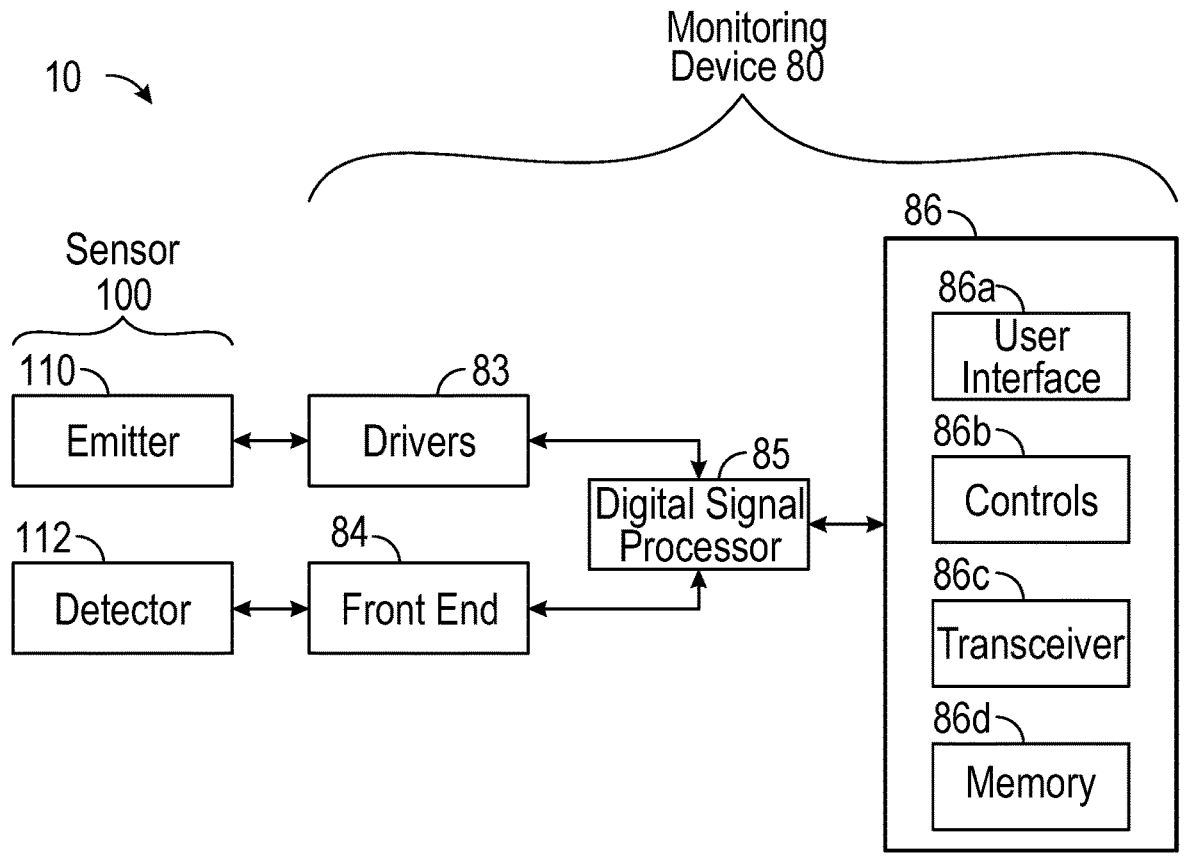
FIG. 1B illustrates a block diagram of a monitoring system in accordance with aspects of this disclosure.

The sensor 100 can be or comprise one or more emitters (such as one, two, three, four, five, or six or more emitters) and/or one or more detectors (such as one, two, three, four, five, or six or more detectors) which can be utilized to obtain information indicative of one or more physiological parameters. For example, with reference to FIG. 1B, the sensor 100 can include an emitter 110 and a detector 112. As shown in FIG. 1B, the monitoring device 80 can include a front end 84 (which can also be referred to as a front end interface), drivers 83, a digital signal processor (DSP) 85, and an input or output device 86. In some implementations, the drivers 83 and/or front end 84 can be comprised by and/or form part of the sensor interface 81 discussed above. The output device 86 can include a user interface 86a, controls 86b, a transceiver 86c, and/or a memory device 86d. Although FIG. 1B illustrates only one emitter and one detector, as discussed previously, the sensor 100 can include multiple emitters 110 and/or multiple detectors 112. For ease of reference, the one or more emitters may be individually or collectively referred to as emitter 110 and the one or more detectors can be individually or collectively referred to as detector 112.

The DSP 85 can communicate with and/or control the emitter 110 via drivers 83, and the DSP 85 can communicate with the detector 112 via a front end 84. For example, the emitter 110 can emit light, and the detector 112 can sense at least a portion of the light after it interacts with tissue of a subject and can generate one or more signals indicative of the sensed light. The generated signal(s) can be indicative of an intensity of light reflected, refracted, scattered, absorbed, or transmitted at a tissue site. The drivers 83 can convert digital control signals into analog drive signals capable of driving the emitter 110 to illuminate the tissue site. Light emitted by the emitter 110 can have an infrared (IR), near infrared (NIR), red, ultra-violet (UV), visible, or other wavelength. The detector 112 can generate one or more composite analog light intensity signals responsive to light detected by the detector 112 after attenuation, reflection, refraction, scattering, absorption, etc., at the tissue site. The emitter 110 and detector 112 can be positioned at various locations on or around a tissue site when the sensor 100 is in use. For example, when the tissue site is a finger, toe, wrist, or the like, the emitter 110 or the detector 112 can be positioned on a top side, on a bottom side, or on the right and/or left sides of the finger when the sensor 100 is in use.

The front end 84 can convert the one or more composite analog light intensity signals from the detector 112 into digital data and input the digital data into the DSP 85. The digital data from the front end 84 can correspond to and/or be indicative of at least one of a plurality of physiological parameters such as any of those described herein. For example, the digital data from the front end 84 can be representative of a change in the absorption of particular wavelengths of light as a function of the changes in the tissue site resulting from pulsing blood.

The DSP 85 can include one or more data or signal processors configured to execute one or more programs for determining physiological parameters from input data. The DSP 85 can perform operations that include calculating and/or outputting one or more physiological measurements. In some cases, the DSP 85 can receive multiple signals from the sensor 100. For example, the sensor 100 may include a multi-emitter, multi-detector, and/or movable arrangement, such as any of those described herein. In some such cases, the DSP 85 can obtain multiple signals, determine an estimation of a physiological parameter for each, some, or all received signals, and can use any of various arbitration techniques to select or to combine the estimations, or to determine a confidence parameter. The operations performed by the DSP 85 can be implemented in software, firmware or other form of code or instructions, or logic or other hardware, or a combination of the above.

The DSP 85 can compare or analyze one or more of the determined parameters (for instance, at least two of the determined parameters or one determined parameter and a previous or model parameter) to adjust how a parameter is measured or calculated to make the measured parameter more accurate or reliable, to adjust a sensor to make the measured parameter more accurate or reliable, to calculate, derive or determine an accuracy or a confidence value of a measured parameter, to isolate a parameter, or to determine another parameter based on the one or more parameters.

The user interface 86a can include a numerical or graphical display that provides readouts of measures or parameters, trends and bar graphs of measures or parameters, visual indications of measures or parameters, visual indicators like LEDs of various colors that signify measurement magnitude, or device management interfaces, which can be generated by LEDs, LCDs, or CRTs, for example. The user interface 86a can include an audible output device that provides readouts or audible indications of measures or parameters. The user interface 86a can include one or more input devices like a keypad, touch screen, pointing device, voice recognition device, and computer that can be used to supply control or configuration data, such as initialization settings, from the user interface 86a to an instrument manager. In some implementations, the user interface 86a can be an interface for devices as well as users.

The controls 86b can be outputs to medical equipment, such as drug administration devices, ventilators, or fluid IVs, so as to control the amount of administered drugs, ventilator settings, or the amount of infused fluids. The monitoring device 80 can use the controls 86b to automatically treat a patient (for instance, provide fluid to the patient, provide medication to the patient, turn on a fan to cool the patient, or adjust a temperature of a room to heat or cool the patient) in response to determining that the patient may benefit from treatment.

The transceiver 86c can transmit information via an antenna about operation of the monitoring device 80 to an electronic device or receive control or configuration data for operating the monitoring device 80. The transceiver 86c can, for example, communicate via a computer network or intermediary device or directly with the electronic device using electromagnetic radiation. The transceiver 86c can be configured to wirelessly communicate with a separate device. As another example, the transceiver 86c can be configured to wirelessly transmit processed and/or unprocessed physiological information obtained by the sensor 100 and/or monitoring device 80. The transceiver 86c can be configured to use any of a variety of wireless protocols, such as Wi-Fi (802.11x), Bluetooth®, ZigBee®, Zwave®, cellular telephony, infrared, near field communication (NFC), RFID, satellite transmission, proprietary protocols, combinations of the same, and the like.

The memory device 86d can be used to store information about operation of the monitoring device 80. This information can, for example, include readouts of measures or parameters, trends and bar graphs of measures or parameters, visual indications or indicators. The memory device 86d can be used to store data such as information obtained from the sensor 100 and/or determined by the monitoring device 80 based on such information. The memory device 86d can be or include, including without limitation, dynamic and/or static random access memory (RAM), programmable read-only memory (PROM), erasable programmable read-only memory (EPROM), electrically erasable programmable read-only memory (EEPROM), and the like.

One or more of the components relating to signal acquisition or processing (for example, front end 84, drivers 83, DSP 85, etc.) can be incorporated into one or more connecting cables, the sensor itself, or are otherwise closer to the sensor sites. As such, the monitoring device 80 can include primarily the input or output device 86. In addition, some of the components are illustrated as separate units but can be combined. By reducing the number of components included in the monitoring device 80, the monitoring device 80 can be smaller in size or more portable, which can be more convenient for home or spot-check use. Although not illustrated in FIGS. 1A-1B, the monitoring device 80 and/or cables connecting the monitoring device 80 to the sensor(s) 100 can further include one or more outputs that supply one or more signals from the sensor 100 to one or more other electronic devices for further processing.

Figure 1C:
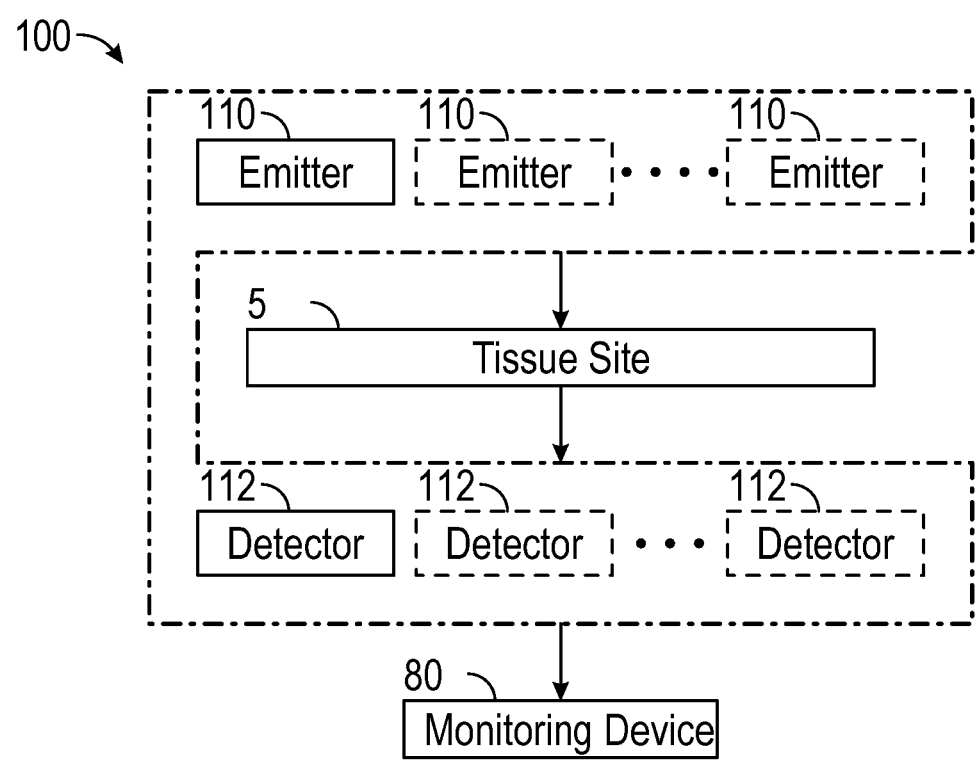
FIG. 1C illustrates a block diagram of a sensor in accordance with aspects of this disclosure.

FIG. 1C shows an illustrative schematic diagram of the sensor 100. As shown, the sensor 100 can include one or multiple emitters 110 and one or multiple detectors 112. The sensor 100 can include one, two, three, four, five or six or more emitters 110 and/or can include one, two, three, four, five or six or more detectors 112. While FIG. 1C shows an illustrative arrangement of emitter(s) 110 and detector(s) 112 operating in a transmittance configuration where at least a portion of the light emitted by the emitter(s) 110 are detected by the detector(s) 112 after being transmitted through the tissue site 5, sensor 100 could alternatively (or additionally) be configured for reflectance configuration(s) where light is emitted by emitter(s) 110 and detected by detector(s) 112 after reflected from the tissue site 5 or a portion thereof.

The emitter 110 can be a light-emitting diode (LED). The emitter(s) 110 can each emit light of the same or different wavelengths. The emitter(s) 110 can emit light of different wavelengths in sequence with only one emitter emitting light at a given time, thereby forming a pulse sequence. For example, the emitter(s) 110 can be modulated or selectively activated so that only one emitter 110 (or a subset of emitters) is emitting light at a given time. For example, a first emitter can be activated for a first quarter cycle and off for the remaining three-quarters cycle; and a second emitter can be activated for a third quarter cycle and off for the remaining three-quarters cycle. In this way, the emitters can be cycled on and off alternately, in sequence, with each only active for a quarter cycle and with a quarter cycle separating the active times. Alternative activation sequences for the emitter(s) 110 may be used to provide a time-multiplexed signal from the detector 112 allowing separation of emitter signals.

The detector 112 can include one or more photodetectors, photodiodes, phototransistors, or the like. Details of an exemplary photodetector that can be utilized for detector 112 are described in U.S. Pat. No. 9,277,880, the disclosure of which is incorporated by reference herein in its entirety. The detector 112 can detect the light emitted by the emitter 110 after the light is attenuated by tissue of the tissue site 5. The detector 112 can generate an electrical signal based on the detected light from the emitter(s) 110. The detector 112 can detect the light from the emitter(s) 110 after the light is attenuated by tissue, for example, between the detector(s) 112 and the emitter(s) 110. Such tissue can be located at a measurement site, such as a cephalic site. Additionally or alternatively, the measurement site can be a peripheral site. The detector(s) 112 can generate an electrical signal based on the detected light from the emitter(s) 110. The signals of the sensor 100 can be provided to the processor 82 (for example, via the sensor interface 81) for processing and determining measurements of physiological parameters.

The signals of the sensor 100 (such as the signal of the emitted light from the emitter(s) 110 and the signal of the detected light from the detector(s) 112) can be fed into the processor 82. The processor 82 can process raw or minimally processed data to generate one or multiple measurements or estimations of physiological parameters. The processor 82 can additionally or alternatively process an output of one detector independently of the output of another detector to produce two measurements of the physiological parameter respectively. For example, the processor 82 may determine an estimation of a physiological parameter for each detector signal such that the number of physiological parameter estimates corresponds to the number of detector(s) 112. As another example, the processor 82 may combine sensor data from at least two detector signals to determine an estimation of a physiological parameter.

The processor 82 can determine a final measurement of the physiological parameter based on one or more signals from one sensor 100 or one or more signals from multiple sensors 100. The final measurement can be an average, weighted average, linear combination, etc. of those measurements, or others. The signal processor can also compare the single measurement from the combined data with the measurements from the individual sensors to obtain additional information about the patient.

Although the monitoring device 80 of system 10 of FIGS. 1A-1B is described above as including components that allow for processing and/or determination of physiological parameters, in some implementations, sensor 100 can additionally or alternatively include similar components. For example, in some implementations, sensor 100 includes a processor that can be similar or identical to processor 82 that can process and/or determine one or more physiological parameters based on one or more signals generated by the detector(s) 112 and based on light emitted by emitter(s) 110 attenuated through tissue site 5 of a subject. In some implementations, sensor 100 can transmit such determined physiological parameters to a separate device (such as monitoring device 80), for example, via wired or wireless methods. In some implementations, sensor 100 is configured to wirelessly transmit, via a transceiver similar or identical to transceiver 86c, physiological parameters to a separate device.

Any of the sensors discussed herein, such as sensor 200, 300, 400, 500, 600, 700, 800, and/or 900 can include any of the features described above with respect to sensor 100, and any of sensor 200, 300, 400, 500, 600, 700, 800, and/or 900 can be configured to interact with a monitoring device such as monitoring device 80 in a manner similar or identical as discussed above with respect to sensor 100 and monitoring device 80.

Any of the sensors discussed herein, such as sensor 100, 200, 300, 400, 500, 600, 700, 800, and/or 900 can be utilized in systems, sensor assemblies, and/or devices similar or identical to those discussed in U.S. Pat. Pub. No. 2020/0138288, the disclosure of which is incorporated by reference herein in its entirety.

Some of the figures of the present disclosure illustrate various emitters and/or detectors of sensors in dotted lines to better illustrate surrounding portions of the sensor or portions of a subject's body proximate the sensor. In various implementations of sensors described herein, the emitter(s) and/or detector(s) can be positioned on interior portions, exterior portions, and/or within (for example, within a thickness of) the sensor (for example, of a body portion of the sensor).

Multiple Path Lengths

There are many sources of potential measurement error introduced to pulse oximetry systems. Some such sources of error include the pulse oximetry system's electronic components, including emitters and detectors, as well as chemical and structural physiological differences between subjects (e.g., patients). Another source of measurement error is the particular tissue geometry of a measurement site. For example, the particular tissue geometry can affect the scattering of photons as the photons pass through the subject's tissue (arterial blood) and arrive at the sensor's light detector. To improve the accuracy or reliability, a system can obtain multiple estimations of the physiological parameter and can use any of various arbitration techniques to select or to combine the estimations, or to determine a confidence parameter.

As described, the sensors described herein can include an emitter and a detector. The emitter can emit light into tissue of a patient and the detector can receive the light after it has been attenuated by the tissue. Beer's Law relates the attenuation of light to properties of a material. In particular, Beer's law states that absorbance of a material is proportional to the concentrations of the attenuating species in the material sample. The relationship between these parameters is expressed in Equation 1 below:

$$A = \varepsilon * b * c \tag{Equation 1}$$

where A is the absorbance of the material at a given wavelength of light, $\varepsilon$ is the molar absorptivity or extinction coefficient (L mol$^{-1}$ cm$^{-1}$), unique to each molecule and varying with wavelength, b is the length of the light path through the material (cm) (generally referred to as path length), and c is the concentration of an analyte of interest (mol L$^{-1}$).

In general, the path length corresponding to a particular emitter/detector pair varies based on the geometry of the tissue that is illuminated, as well as the distance between or orientation of the emitter and detector. Consequently, different emitter/detector pairs typically obtain measurements associated with different path length. Similarly, the path length associated with an emitter/detector pair will likely change if the position of the emitter or detector is changed relative to the tissue site. In some cases, arranging or configuring the sensor to obtain measurements that relate to different path lengths and/or different tissue geometries can reduce the likelihood of a measurement error across all measurements, thereby improving the accuracy, reliability, or robustness of the sensor.

Systems, methods, and devices disclosed herein can improve the accuracy, reliability, and/or robustness of physiological parameter estimations by measuring light of diverse path lengths. For example, a system can include multiple sensors that are placed at different measurement sites, such as on different fingers or different portions of the same finger. Some implementations of monitoring systems disclosed herein can simultaneously or concurrently receive measurements from multiple measurement sites. As another example, a particular sensor may include multiple emitters and/or multiple detectors, which can be utilized to obtain measurements corresponding to different path lengths. As another example, a particular sensor or component thereof may be configured to move to alternate positions to vary the path length associated with its measurements.

Multi-Detector Arrangements

In some implementations, a sensor can include an emitter and a plurality of detectors and the sensor can output signals corresponding to varying path lengths of light detected by each of the detectors. The path length between each of the detectors and the emitter can be different depending on the arrangement of the detectors in the sensor, and such differential path length can result in variable output signals from each of the detected based on detected light. The sensor, and/or a monitoring device connected to the sensor, can use the signals generated by the detectors to determine estimations of a physiological parameter. In this way, at least some of the different estimations of a physiological parameter can correspond to different path lengths, which can improve the accuracy, reliability, and/or robustness of a physiological parameter determination. For example, using any of various arbitration techniques, the sensor, and/or a monitoring device connected to the sensor, can select or combine the estimations or can determine a confidence parameter associated with an estimation. Furthermore, systems, methods, or devices disclosed herein can utilize particular distances, angles, or spatial configurations between a set of detectors and/or between an emitter and a particular detector to further improve an accuracy, reliability, and/or robustness of physiological parameter determinations.

Figure 2A:
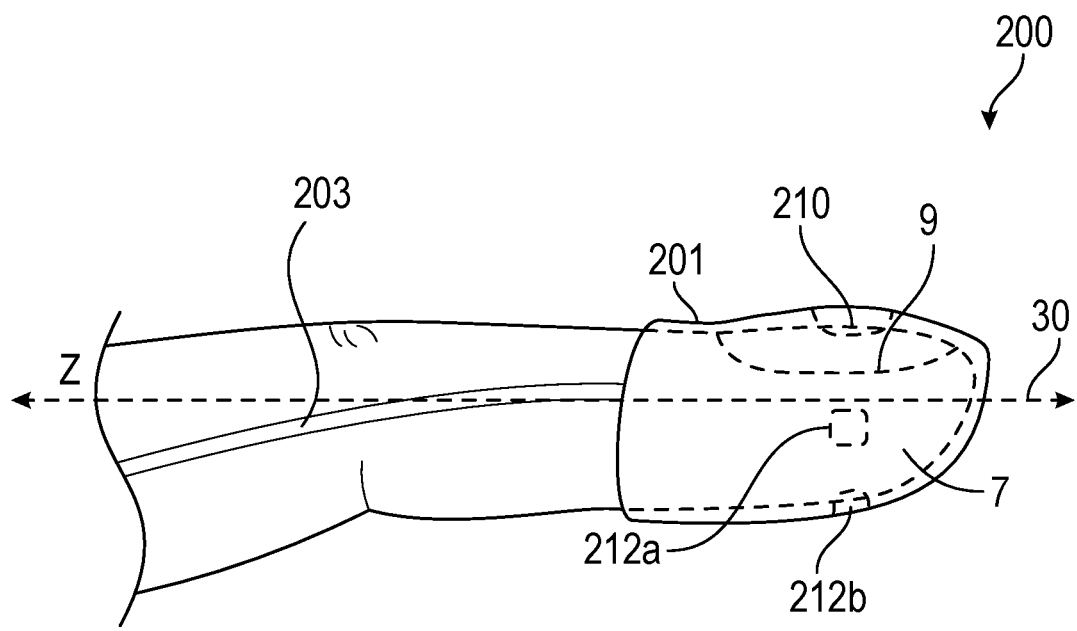
FIG. 2A illustrates an embodiment of a sensor in accordance with aspects of this disclosure.
Figure 2B:
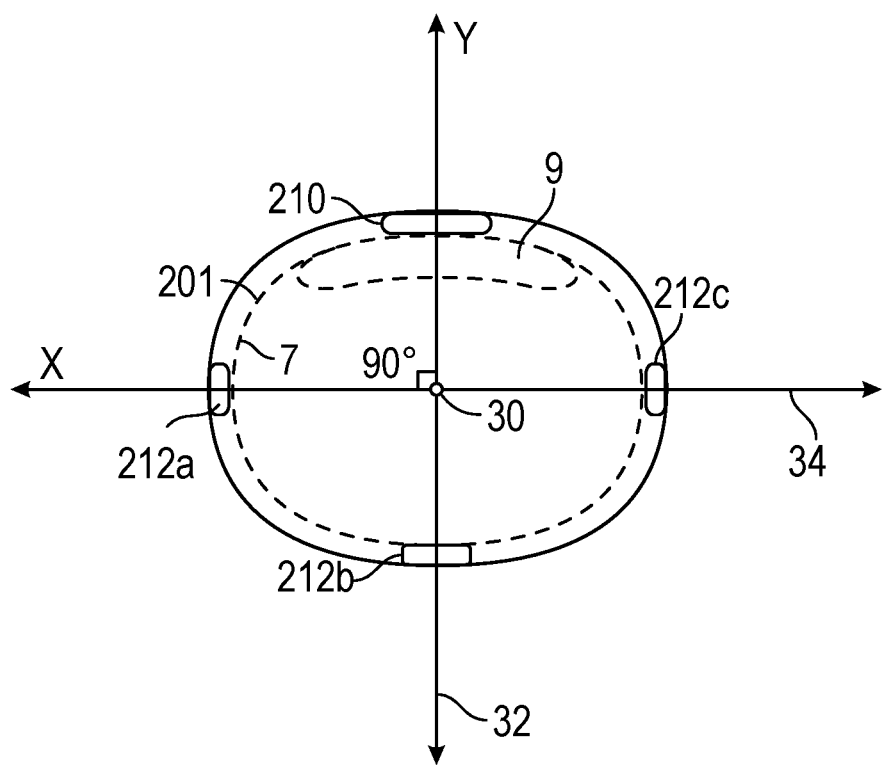
FIG. 2B illustrates a cross-sectional view of a portion of the sensor of FIG. 2A in accordance with aspects of this disclosure.

FIG. 2A shows an illustrative multi-detector arrangement of a sensor 200, and FIG. 2B illustrates a cross-sectional representational view of the arrangement of FIG. 2A. As shown, the multi-detector arrangement includes an emitter 210 and multiple detectors 212a, 212b, 212c that are distributed in an area proximate the tissue site. The emitter 210 and detectors 212a, 212b, 212c are shown in dotted lines in FIG. 2A and are shown in solid lines in FIG. 2B. The representation of the emitter 210 and the detectors 212a, 212b, 212c in solid or dotted lines is not meant to be limiting but is meant for illustrative purposes. Furthermore, the representation of the locations of the emitter 210 and/or detectors 212a, 212b, 212c in FIGS. 2A-2B is not meant to limiting of the location of the emitters 210 and/or detectors 212a, 212b, 212c. The emitter 210 and/or detectors 212a, 212b, 212c can be positioned on interior portions, exterior portions, and/or within (for example, within a thickness of) the sensor (for example, of a body portion of the sensor). The sensor 200 can be configured to be worn and/or to secure to a tissue site on a subject. For example, the sensor 200 can be configured to secure to a finger of a user. Additionally or alternatively, the sensor 200 can be configured to secure to another portion of the user's body, such as a toe, an ear, nose, arm, wrist, among others. Accordingly, while sensor 200 may be described below in the context of a finger, the location of securement of the sensor 200 to a subject is not so limited.

With reference to FIG. 2A, the sensor 200 can comprise a body portion 201 configured to secure and/or operably position the detectors 212a, 212b, 212c and the emitter 210, for example, relative to a finger of the subject. In some cases, the body portion 201 can conform and/or secure to and/or around the finger of the subject. The body portion 201 can comprise one or more materials, for example, a fabric material. The body portion 201 can comprise a sleeve, for example, that is configured to slide over a finger or portion of a finger (e.g., fingertip). The emitter 210 and/or detectors 212a, 212b, 212c can be secured to an exterior surface or interior surface of the body portion 201, or alternatively, can be positioned within the body portion 201 (e.g., can be positioned within or partially within a thickness of the body portion 201).

The spacing between or the arrangement of the detectors 212a, 212b, 212c and/or the emitter 210 can vary across implementations of the sensor 200. In some cases, the detectors 212a, 212b, 212c and/or the emitter 210 can be positioned or spaced (e.g., circumferentially) to maximize a difference between the tissues sampled by each of the detectors 212a, 212b, 212c. In some cases, the detectors 212a, 212b, 212c can be equally spaced at least partially around the tissue site when the sensor 200 is in use, for example, when the body portion 201 is secured to a finger. For example, the detectors 212a, 212b, 212c can be equally spaced from each other and/or the emitter 210 when the sensor 200 is in use. In some cases, the detectors 212a, 212b, 212c can be unequally spaced about the tissue site when the sensor 200 is in use. For example, the arrangement or spatial distribution of emitter 210 and the detectors 212 can be random or arbitrary.

As mentioned above, the sensor 200 can include and operably position an emitter 210 and multiple detectors 212a, 212b, 212c around a tissue site (e.g., a fingertip). For example, the sensor 200 can include a body portion 201 that can arrange the emitter 210 and the detectors 212a, 212b, 212c circumferentially around a perimeter of a cross-section through the fingertip and/or through the body portion 201 when the sensor 200 is in use. The relative positions and/or arrangement of the emitter 210 and detectors 212a, 212b, 212c can be described with respect to an axis extending through the body portion 201 or a portion thereof when the body portion 201 is secured to a portion of the subject's body (e.g., a finger) and/or when the body portion 201 is not secured to a portion of the subject's body. Additionally or alternatively, the relative positions and/or arrangement of the emitter 210 and detectors 212a, 212b, 212c can be described with respect to a longitudinal axis 30 (e.g., angular displacement with respect to rotation about a longitudinal axis 30) of the tissue site (e.g., a fingertip). In the figures, axis 30 is also referenced as a "Z" axis and shown along with mutually orthogonal "X" and "Y" axes (also labeled 34 and 32 respectively). For instance, in the example of FIG. 2A, when the sensor 200 is positioned around and/or secured to a fingertip, the emitter 210 is positioned at (e.g., above) the nail-bed 9, and detectors 212a, 212c are positioned opposite each other relative to the fingertip and are each offset approximately 90 degrees (circumferentially) from the emitter 210 with respect to the longitudinal axis 30 and/or an axis that extends through at least a portion of the body portion 201. Further, in the example of FIG. 2A, the sensor 200 includes a third detector 212b positioned opposite the emitter 210 relative to the fingertip when the body portion 201 is secured thereto, which is offset approximately 180 degrees (circumferentially) from the emitter 210 with respect to the longitudinal axis 30 (and/or an axis extending through at least a portion of the body portion 201). As shown, the third detector 212b can be offset approximately 90 degrees (circumferentially) from each of the detectors 212a, 212c. The emitter 210 and detectors 212a, 212b, 212c can be located on or along the same plane (e.g., a plane defined by X axis 34 and Y axis 32, as shown in FIGS. 2A-2B). For example, emitter 210 and detectors 212a, 212b, 212c can be operably positioned by the body portion 201 along a plane that can define a cross-section through the body portion 201, for example, when the body portion 201 is secured to the finger. Alternatively, in some implementations, the emitter 210 and one or more of detectors 212a, 212b, 212c can be operably positioned by the body portion 201 to not be on a common plane when the body portion 201 is secured to the finger. As illustrated in FIG. 2A, a fingertip 7 and the nail-bed 9 (which can also be referred to as a "nail") can be received and/or covered by the body portion 201 of the sensor 200 when the sensor 200 is in use. Fingertip 7 and nail-bed 9 are illustrated in dotted lines in FIGS. 2A-2B to show respective positions relative to the sensor 200 when the sensor 200 is secured to the finger.

Although the emitter 210 and detectors 212a, 212b, 212c are illustrated as being spaced (circumferentially) approximately 90 degrees from each other relative to the longitudinal axis 30 (e.g., as shown in FIG. 2B), this should not be construed as limiting. In some cases, the spacing relative to the longitudinal axis 30 can vary based on the total number of emitters and detectors in sensor 200. For example, given n number of emitters and detectors in sensor 200, each emitter and detector can be spaced from another emitter or detector by 360/n degrees. In some cases, detectors 212a, 212b, 212c of sensor 200 are equally spaced from each other regardless of the position of the emitter 210. For example, each of detectors 212 can be spaced approximately 5, 10, 20, 30, 45, 60, or 75 degrees from other detectors 212a, 212b, 212c, or any range defined by any of such values or any range of value between any of these values.

In some implementations, detectors 212a, 212c that are positioned at similar angle magnitudes (e.g., 90 degrees) relative to the emitter 210 (circumferentially) about longitudinal axis 30 can capture similar tissue geometry. For instance, detectors 212a, 212c on either side of (e.g., right and left side) the subject's fingertip 7 can capture similar tissue geometry. In some cases, such detectors 212a, 212c positioned at similar angle magnitudes relative to the emitter 210 on either side that capture similar geometry may be used to determine a single physiological parameter.

In some implementations, sensor 200 includes and/or is configured to connect to a cable 203. Cable 203 can facilitate communication between sensor 200 and a separate device, such as a monitoring device similar or identical to monitoring device 80 discussed above. However, in some implementations, sensor 200 does not include a cable, for example, where sensor 200 is configured to wirelessly communicate with separate devices.

Figure 2C:
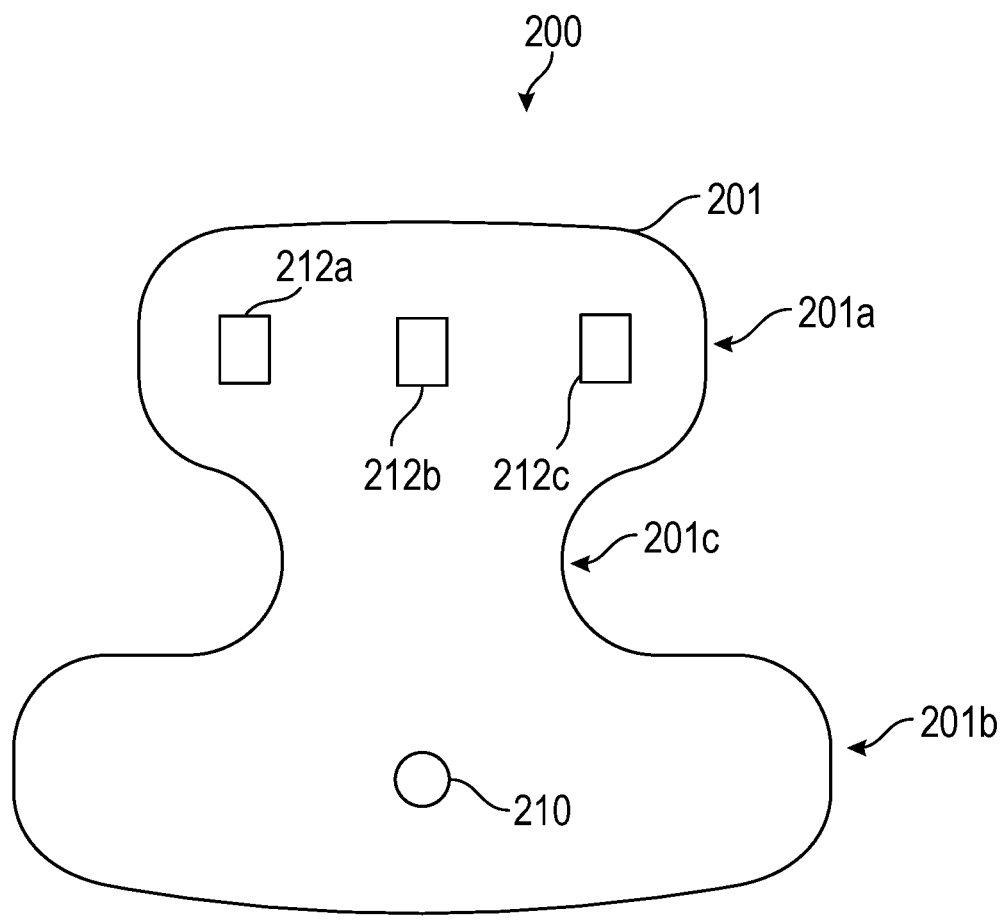
FIG. 2C illustrates the sensor of FIGS. 2A-2B in a first configuration in accordance with aspects of this disclosure.

As discussed above, sensor 200 can be configured to secure to a finger of a subject and/or another portion of the subject's body. As also discussed above, sensor 200 can include a body portion 201 that can secure the sensor 200 at least partially to a portion of the subject's body and that can operably position emitter 210 and detectors 212a, 212b, 212c. In some implementations, body portion 201 is a sleeve that can slide and/or be otherwise positioned over a portion of the subject's body (e.g., a finger). In some implementations, body portion 201 is configured to be wrapped around a portion of the subject's body. For example, in some implementations, sensor 200 is a tape sensor. As another example, in some implementations, portions of the body portion 201 are configured to wrap around a subject's finger and secure to other portions of the body portion 201. FIG. 2C illustrates an example implementation of body portion 201 of sensor 200. Body portion 201 can include a first portion 201a, a second portion 201b, and a third or intermediate portion 201c that can connect and be positioned between the first and second portions 201a, 201b. First portion 201a can be or represent a detector-side and/or a detector portion of the sensor 200 and/or body portion 201. Second portion 201b can be or represent an emitter-side and/or emitter portion of the sensor 200 and/or body portion 201. In some implementations, the intermediate portion 201c is smaller (for example, narrower) than one or both of portions 201a, 201b. FIG. 2C illustrates sensor 200 in a first configuration where the body portion 201 is substantially flat and not secured to a subject's finger. FIG. 2C illustrates locations of the emitter 210 and detectors 212a, 212b, 212c in such first configuration. In such first configuration, the emitter 210 can be aligned with one of the detectors (for example, detector 212b as shown) and/or the detectors 212a, 212b, 212c can be aligned with one another.

To secure the sensor 200 to a subject's finger, the finger can be positioned over the first portion 201a, the second portion 201b can be wrapped around a tip of the finger, and portions of the first and second portions 201a, 201b can be secured to one another, for example, via adhesive securement and/or mechanical securement (for example, via hook and loop fastener type engagement). In such manner, body portion 201 can be transitioned from a first configuration where it is flat and/or not secured to the finger (see FIG. 2C) to a second configuration where it is secured to the finger (see FIG. 2A-2B). In some implementations, when body portion 201 is in such second configuration, a cross-section of body portion 201 is rounded (see FIG. 2B).

It is to be understood that sensor 200 can be secured to a finger in a variety of ways. For example, body portion 201 can be secured to a finger such that the emitter 210 is positioned at a top side or a bottom side of the finger and detector 212b is positioned at a top side or a bottom side of the finger. In some cases, the sensor 200 (for example, body portion 201) can be sized and/or shaped such that, when positioned over a fingertip, sensor 200 (for example, body portion 201) does not cover the subject's knuckles.

Figure 3A:
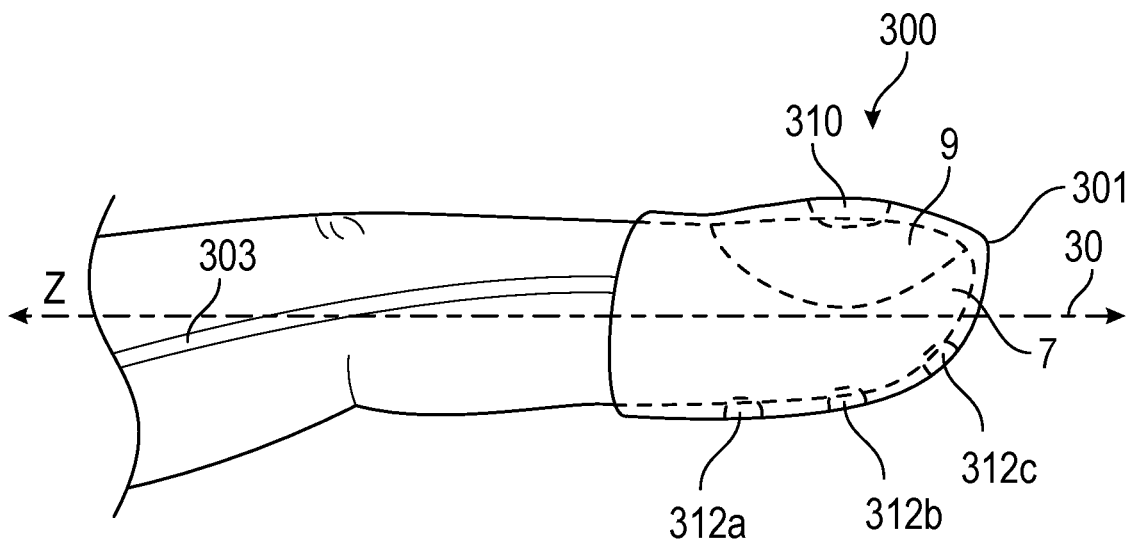
FIG. 3A illustrates another embodiment of a sensor in accordance with aspects of this disclosure.
Figure 3B:
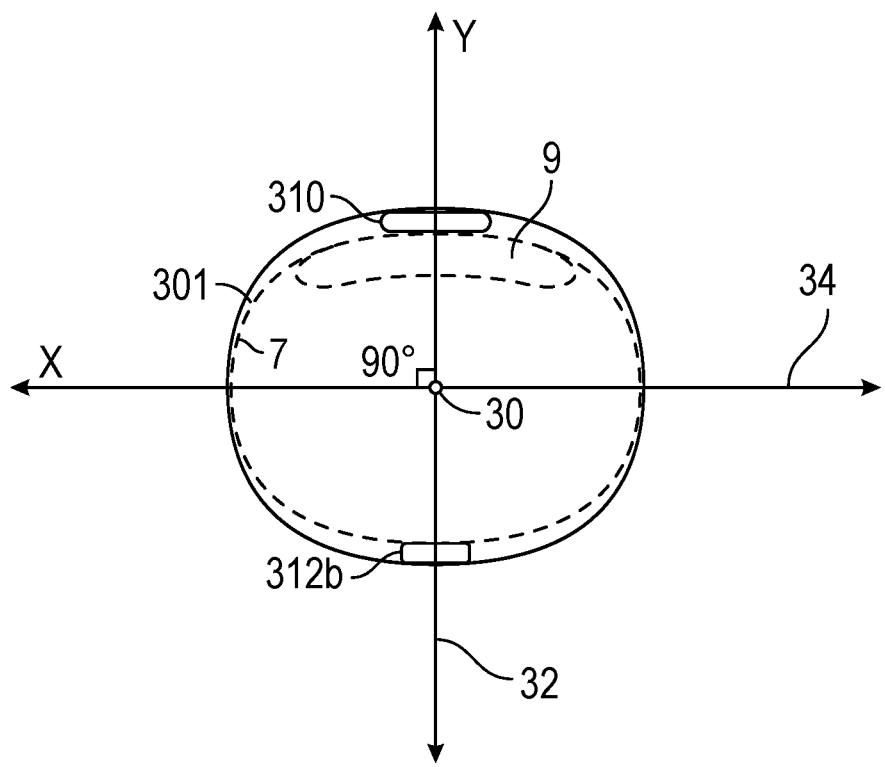
FIG. 3B illustrates a cross-sectional view of a portion of the sensor of FIG. 3A in accordance with aspects of this disclosure.

FIG. 3A shows another illustrative multi-detector arrangement of a sensor 300 and FIG. 3B illustrates a cross-sectional view of the arrangement of FIG. 3A. Similar to the sensor 200 of FIG. 2B, the sensor 300 of FIG. 3A can include an emitter 310 and multiple detectors 312a, 312b, 312c. The emitter 310 and detectors 312a, 312b, 312c are shown in dotted lines in FIG. 3A and are shown in solid lines in FIG. 3B. The representation of the emitter 310 and the detectors 312a, 312b, 312c in solid or dotted lines is not meant to be limiting but is meant for illustrative purposes. Furthermore, the representation of the locations of the emitter 310 and/or detectors 312a, 312b, 312c in FIGS. 3A-3B is not meant to limiting of the location of the emitters 310 and/or detectors 312a, 312b, 312c. The emitter 310 and/or detectors 312a, 312b, 312c can be positioned on interior portions, exterior portions, and/or within (for example, within a thickness of) the sensor (for example, of a body portion of the sensor).

In this example, the detectors 312a, 312b, 312c are operably positioned by a body portion 301 of the sensor 300 to be generally aligned with respect to each other along a bottom side of the subject's fingertip 7 and each are circumferentially offset approximately 180 degrees from the emitter 310 with respect to the longitudinal axis 30 when the sensor 300 is in use (and/or with respect to an axis extending through at least a portion of body portion 301). The detectors 312a, 312b, 312c can be spaced apart from one another along a length of body portion 301 of the sensor 300, for example, as shown in FIG. 3A. In some implementations, sensor 300 includes a cable 303. Cable 303 can be similar or identical to cable 203 discussed above. Sensor 300 can be worn and/or secured to a portion of a subject's body in a similar or identical manner as that described above with reference to sensor 200. Fingertip 7 and nail-bed 9 are illustrated in dotted lines in FIGS. 3A-3B to show respective positions relative to the sensor 300 when the sensor 300 is secured to the finger.

Sensor 300 can include a body portion 301 that can be similar or identical to body portion 201 of sensor 200. In some implementations, body portion 301 is a sleeve that can slide and/or be otherwise positioned over a portion of the subject's body (e.g., a finger). In some implementations, body portion 301 is configured to be wrapped around a portion of the subject's body. For example, in some implementations, sensor 300 is a tape sensor. As another example, in some implementations, portions of the body portion 301 are configured to wrap around a subject's finger and secure to other portions of the body portion 301.

Figure 3C:
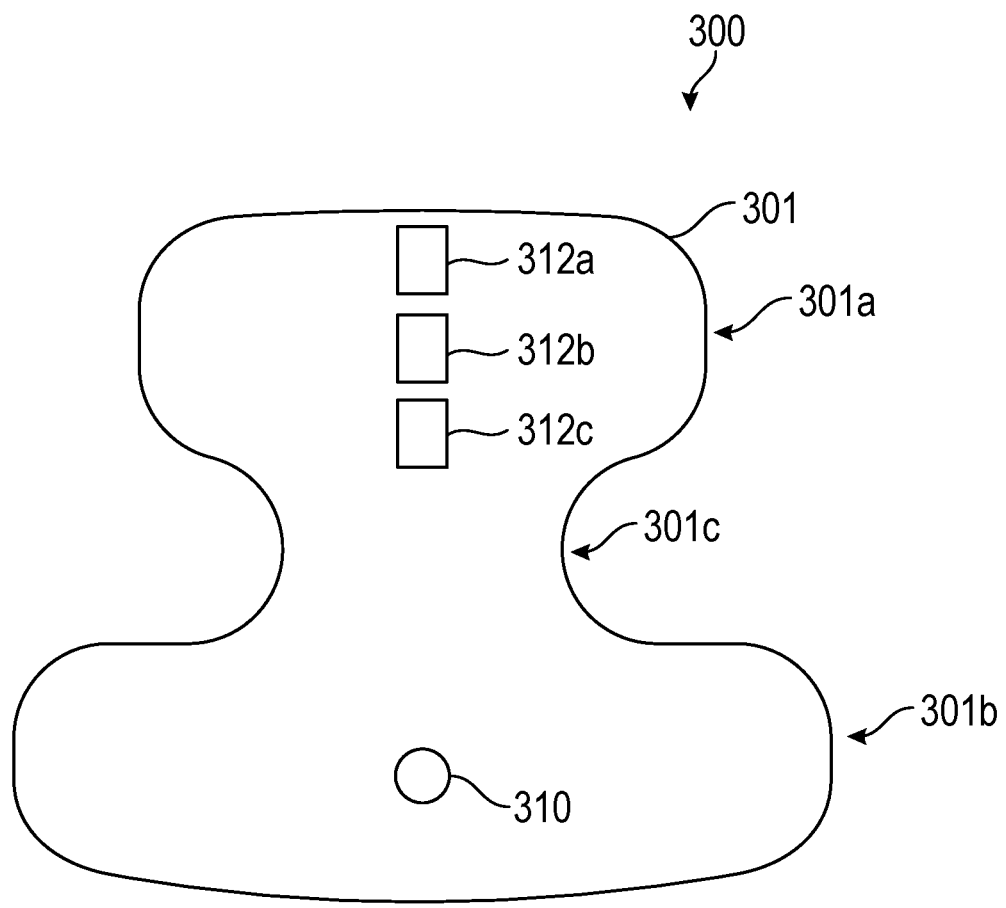
FIG. 3C illustrates the sensor of FIGS. 3A-3B in a first configuration in accordance with aspects of this disclosure.

FIG. 3C shows an illustrative implementation of body portion 301 of sensor 300. Body portion 301 can include a first portion 301a, a second portion 301b, and a third or intermediate portion 301c that can connect and be positioned between the first and second portions 301a, 301b. First portion 301a can be or represent a detector-side and/or a detector portion of the sensor 300 and/or body portion 301. Second portion 301b can be or represent an emitter-side and/or emitter portion of the sensor 300 and/or body portion 301. In some implementations, the intermediate portion 301c is smaller (for example, narrower) than one or both of portions 301a, 301b. FIG. 3C illustrates sensor 300 in a first configuration where the body portion 301 is substantially flat and not secured to a subject's finger. FIG. 3C illustrates locations of the emitter 310 and detectors 312a, 312b, 312c in such first configuration. In such first configuration, the emitter 310 and detectors 312a, 312b, 312c can all be aligned with one another along a common axis.

To secure the sensor 300 to a subject's finger, the finger can be positioned over the first portion 301a, the second portion 301b can be wrapped around a tip of the finger, and portions of the first and second portions 301a, 301b can be secured to one another, for example, via adhesive securement and/or mechanical securement (for example, via hook and loop fastener type engagement). In such manner, body portion 301 can be transitioned from a first configuration where it is flat and/or not secured to the finger (see FIG. 3C) to a second configuration where it is secured to the finger (see FIG. 3A-3B). In some implementations, when body portion 201 is in such second configuration, a cross-section of body portion 301 is rounded (see FIG. 3B).

It is to be understood that sensor 300 can be secured to a finger in a variety of ways. For example, body portion 301 can be secured to a finger such that the emitter 310 is positioned at a top side or a bottom side of the finger and detectors 312a, 312b, 312c are positioned at a top side or a bottom side of the finger. In some cases, the sensor 300 (for example, body portion 301) can be sized and/or shaped such that, when positioned over a fingertip, sensor 300 (for example, body portion 301) does not cover the subject's knuckles.

Although FIGS. 2A and 3A depict only a single sensor 200, 300 attached to a fingertip 7, the number of sensors and the location of measurement sites are not limiting. For example and not by way of limitation, a system may include two, or three or more sensors attached to any of the patient's finger, hand, wrist, arm, face, leg, ankle, foot, toe, ear among other portions of a subject's body. In examples that include multiple sensors, the sensors may be attached to the same or a different measurement site. Furthermore, the number of emitters and/or detectors of a particular sensor can vary across examples. For example, the number of emitters and/or detectors can range from one to twelve.

Figure 4:
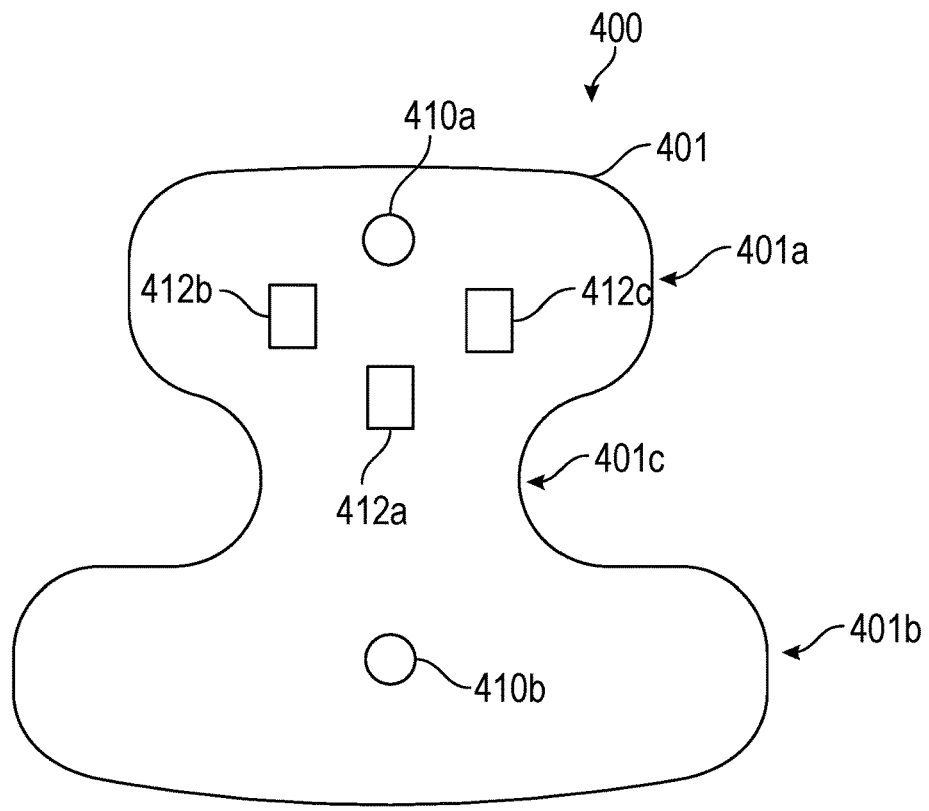
FIGS. 4-5 illustrate configurations of additional embodiments of sensors in accordance with aspects of this disclosure.
Figure 5:
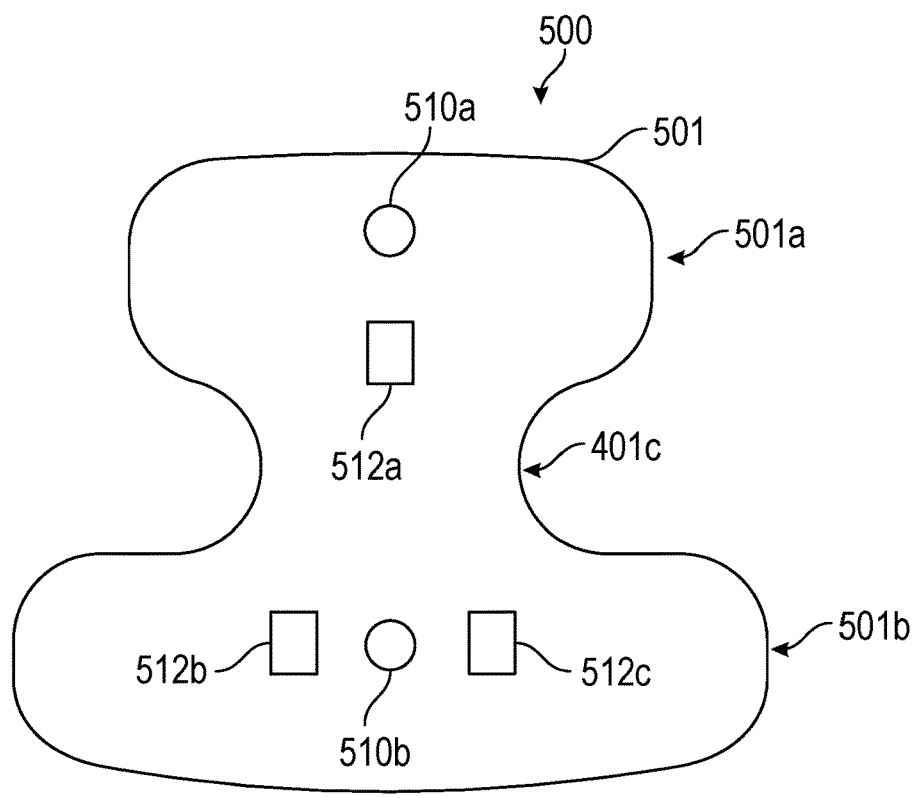

FIGS. 4-5 illustrate example multi-detector arrangements of sensors 400, 500, respectively. Sensors 400, 500 can be similar to sensors 200, 300 in some or many respects. Sensors 400, 500 can be configured to be secured to a portion of a subject's body (e.g., a finger) via wrapping in a similar or identical manner as that discussed above with reference to sensors 200, 300 and FIGS. 2C and 3C. Sensors 400, 500 can include body portions 401, 501, which can be similar or identical to body portions 201, 301 of sensors 200, 300. For example, body portions 401, 501 can each include first, second, and third portions 401a, 501a, 401b, 501b, 401c, 501c that can be similar or identical to first, second, and third portions 201a, 301a, 201b, 301b, 201c, 301c of body portions 201, 301. As shown, sensor 400 can include emitters 410a, 410b and detectors 412a, 412b, 412c and sensor 500 can include emitters 510a, 510b, and detectors 512a, 512b, 512c. FIGS. 4-5 illustrate sensors 400, 500 in a first configuration where sensors 400, 500 are not secured to a finger. Each of sensors 400, 500 can be transitioned to a second configuration where sensors 400, 500 are secured to a finger of a subject in a similar or identical manner as that discussed and shown above with reference to sensors 200, 300 and FIGS. 2A-3C.

With reference to FIG. 4, sensor 400 can include emitter 410b on a second portion 401b of the body portion 401 and an emitter 410a and detectors 412a, 412b, 412c on a first portion 401a of the body portion 401. When body portion 401 is in a first configuration (as shown in FIG. 4), emitter 410b, detector 412a, and emitter 410a can be aligned with one another along a common axis. When body portion 401 is in such first configuration (as shown in FIG. 4), detector 412b and detector 412c can be aligned with one another along a common axis. Body portion 401 can be substantially flat when in such first configuration. When the body portion 401 is in a second configuration (e.g., secured to the finger) emitter 410b can be positioned at a top side of a finger (e.g., adjacent to a nail bed of the finger) and emitter 410a can be positioned at a bottom side of the finger along with detector 412a. Additionally, when the body portion 401 is in such second configuration (e.g., secured to the finger), each of detectors 412b, 412c can be positioned on right and left sides of the finger.

With reference to FIG. 5, sensor 500 can include emitter 510a and detector 512a on first portion 501a of body portion 501 and emitter 510b, detector 512b, and detector 512c on second portion 501b of body portion 501. When body portion 501 is in such first configuration (as shown in FIG. 5), emitter 510a, emitter 510b, and detector 512a can be aligned with one another along a common axis. When body portion 501 is in such first configuration (as shown in FIG. 5), detector 512b, detector 512c, and emitter 510b can be aligned with one another along a common axis. Body portion 501 can be substantially flat when in such first configuration. When the body portion 501 is in a second configuration (e.g., secured to a finger), emitter 510a and detector 512a can be positioned at a bottom side of the finger and emitter 510b can be positioned at a top side of the finger (e.g., adjacent to a nail bed of the finger). Additionally, when the body portion 501 is in such second configuration (e.g., secured to a finger), each of detectors 512b, 512c can be positioned on right and left sides of the finger, for example, offset approximately 90 degrees from emitter 510b with respect to an axis extending through a portion of the body portion 501 and/or an axis extending through a portion of the finger.

As can be understood based on the location and arrangement of the emitters 410a, 410b, 510a, 510b and detectors 412a, 412b, 412c, 512a, 512b, 512c in sensors 400, 500, either of sensors 400, 500 can be configured to facilitate either or both of transmittance and reflectance type pulse oximetry. For example, emitter 410a and detector 412a of sensor 400 can be positioned on a same side of a finger and can be operated in a reflectance mode where at least a portion of the light emitted by emitter 410a is detected by detector 412a after reflecting from at least a portion of the subject's tissue. Further, emitter 410b and detector 412a can be positioned on opposite sides of the finger (for example, top and bottom sides of the finger) and can be operated in a transmittance mode where at least a portion of the light emitted by emitter 410b is detected by detector 412a after being transmitted through at least a portion of the subject's tissue. Sensor 400 can be configured to operate in such transmittance and reflectance modes concurrently or non-concurrently. Emitters 510a, 510b and detector 512a can operate in a similar or identical manner as described above with respect to sensor 400.

It is to be understood that sensors 400, 500 can be secured to a finger in a variety of ways. For example, body portion 401 can be secured to a finger such that the emitter 410a and detector 412a are positioned at a top side or a bottom side of the finger and emitter 410b is positioned at a top side or a bottom side of the finger. As another example, body portion 501 can be secured to a finger such that the emitter 510a and detector 512a are positioned at a top side or a bottom side of the finger and emitter 510b is positioned at a top side or a bottom side of the finger. Although not illustrated in FIGS. 4-5, either of sensors 400, 500 can include a cable similar or identical to cables 203, 303 discussed above. In some cases, the sensors 400, 500 (for example, body portions 401, 501) can be sized and/or shaped such that, when positioned over a fingertip, sensors 400, 500 (for example, body portions 401, 501) do not cover the subject's knuckles.

As described with respect to sensors 200, 300 of FIGS. 2A-2C and 3A-3C, the spacing between or the arrangement of the detectors 412a, 412b, 412c, 512a, 512b, 512c and/or the emitters 410a, 410b, 510a, 510b can vary across embodiments of the sensors 400, 500.

Although illustrated in a conventional elongated surface with opposing wings style/shape, an artisan will recognize from the disclosure herein that the sensors 400, 500 shown in FIGS. 4-5 (and/or sensors 200, 300 shown in FIGS. 2C and 3C) may comprise virtually any shape, including those disclosed in U.S. Pat. No. 6,671,531, entitled "SENSOR WRAP INCLUDING FOLDABLE APPLICATOR," which is hereby incorporated by reference herein.

Figure 6:
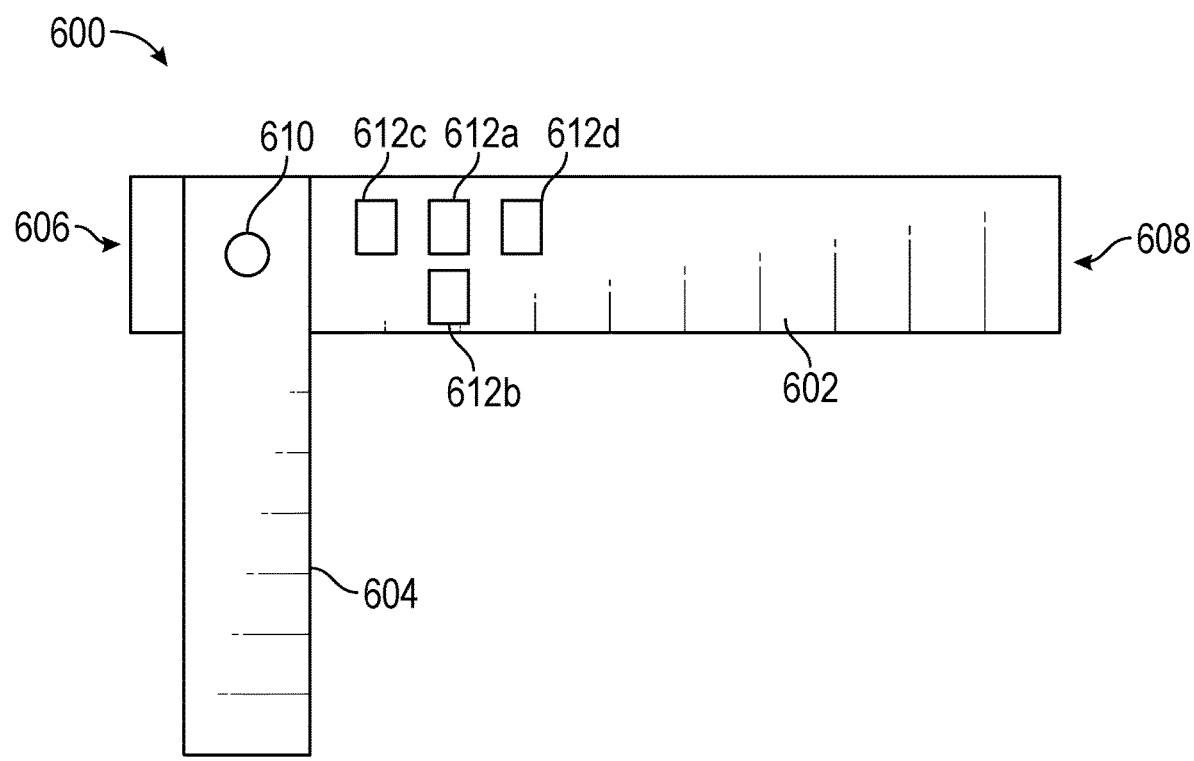
FIG. 6 illustrates another embodiment of a sensor in accordance with aspects of this disclosure.

FIG. 6 illustrates an example multi-detector arrangement of an L-shaped sensor 600. The L-shaped sensor 600 can include emitter 610 and detectors 612a, 612b, 612c, 612d and a sensor tape 602. The L-shaped sensor 600 can include a cable connector for coupling to a sensor cable, which can be plugged into a variety of patient monitoring devices that can provide noninvasive physiological measurements, such as pulse oximeters and multi-parameter monitors. Additional details regarding an L-shaped sensor can be found in U.S. Pub. No. 2020/0037453, entitled "FOLD FLEX CIRCUIT FOR LNOP," which is hereby incorporated by reference herein.

With continued reference to FIG. 6, the sensor tape 602 can cover a portion of the sensor 600. The sensor tape 602 has a sensor end 606 and a free end 608 opposite the sensor end 606. The sensor 600 can additionally include a second sensor tape 604 which can be connected to the sensor tape 602, for example, in between ends 606, 608 of sensor tape 602. The second sensor tape 604 can include a first end connected to the sensor tape 602 and a second end opposite the first end that is "free". The first end of the second sensor tape 604 can be connected to the sensor tape 602 at or near the emitter 610, as illustrated. In some variants, the sensor tapes 602, 604 are transverse (e.g., perpendicular) relative to each other. The emitter 610 can be positioned proximate to the sensor end 606 of sensor tape 602. As illustrated, in some cases, the emitter 610 can be positioned closer to sensor end 606 than to the free end 608 and/or at an intersection of sensor tapes 604 and 602. The sensor tape 602 can extend along a length between the ends 606, 608. The sensor tapes 602, 604 can include an adhesive side and a non-adhesive side opposite the adhesive side. Materials for the adhesive side and the non-adhesive side are not limiting. The sensor tapes 602, 604 can have a rectangular shape with a uniform or varying width and length. The length of the sensor tapes 602, 604 may vary, for example depending on the size of the patient's anatomy.

During use, the L-shaped sensor 600 can be wrapped around a subject's anatomy, such as a foot, a hand, a finger, an ear or a toe, among other locations. In an example in which the subject's anatomy is a finger, the L-shaped sensor 600 can be wrapped such that the emitter 610 is positioned on a nail-bed of the finger, a first detector 612a is positioned on the bottom of the fingertip opposite the emitter 610 relative to the fingertip, a second detector 612b is positioned on the bottom of the fingertip and spaced from the first detector 612a, a third detector 612c is positioned on a side of the fingertip and circumferentially offset approximately 90 degrees from the emitter 610 with respect to a longitudinal axis of the finger, and a fourth detector 612d is positioned on a side of the fingertip opposite the third detector 612c relative to the finger and circumferentially offset approximately 90 degrees from the emitter 610 with respect to a longitudinal axis of the finger.

After a portion of the subject's anatomy (e.g., finger) has been positioned relative to the emitter 610 and detectors 612a, 612b, 612c, 612d, the second sensor tape 602 can be wrapped around the finger or a portion thereof. When wrapped around the finger, the second sensor tape 604 may extend from the sensor end 606 to the free end 608 and can be secured to nearby skin and/or to sensor tape 602. For example, when wrapped around the finger, a first portion of the length of an adhesive side of the second sensor tape 602 can directly contact the subject's skin and a second portion of the length of the adhesive side of the sensor tape 602 can substantially contact the non-adhesive side of the sensor tape 602. The sensor tape advantageously reduces motion-induced electrical noise by positioning and securing the emitter 610 and the detectors 612a, 612b, 612c, 612d to the subject's skin, thereby minimizing movements of the sensor 600 relative to the subject due to subject's movement.

The spacing between and/or the arrangement of the detectors 612a, 612b, 612c, 612d and/or the emitter 610 can vary across embodiments of the sensor 600. In some cases, the detectors 612a, 612b, 612c, 612d and/or the emitter 610 can be positioned or spaced to maximize a difference between the tissues sampled by each of the detectors 612a, 612b, 612c, 612d when the sensor 600 is in use. In some cases, the detectors 612a, 612b, 612c, 612d can be equally circumferentially spaced at least partially around the tissue site when the sensor 600 is in use. For example, the detectors 612a, 612b, 612c, 612d can be equally circumferentially spaced from each other and/or the emitter 610 when the sensor 600 is in use. In some cases, the detectors 612a, 612b, 612c, 612d can be unequally circumferentially spaced about the tissue site when the sensor 600 is in use. For example, the arrangement or spatial distribution of emitter 610 and the detectors 612a, 612b, 612c, 612d can be random or arbitrary. In some cases, the distances between the detectors 612a, 612b, 612c, 612d can change based on a size of the measurement site.

Multi-Emitter Arrangements

Similar to the multi-detector arrangements described herein, a sensor that includes multiple emitters can output signals corresponding to varying path lengths, which can improve the accuracy, reliability, and/or robustness of physiological parameter determination.

Figure 7A:
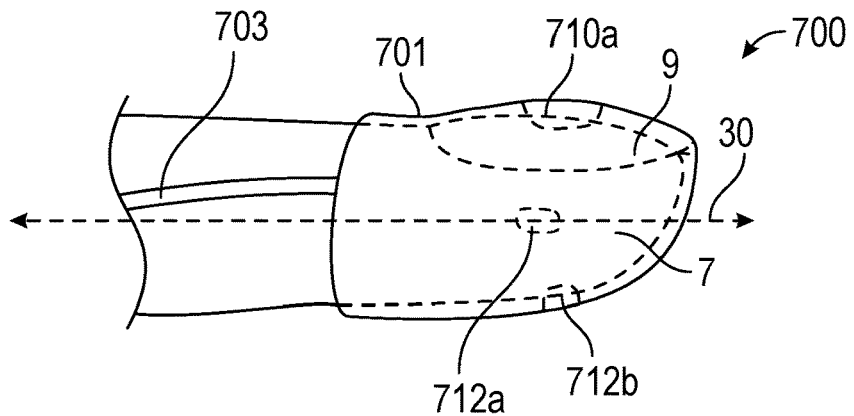
FIGS. 7A-7B illustrate side views of another embodiment of a sensor in accordance with aspects of this disclosure.
Figure 7B:
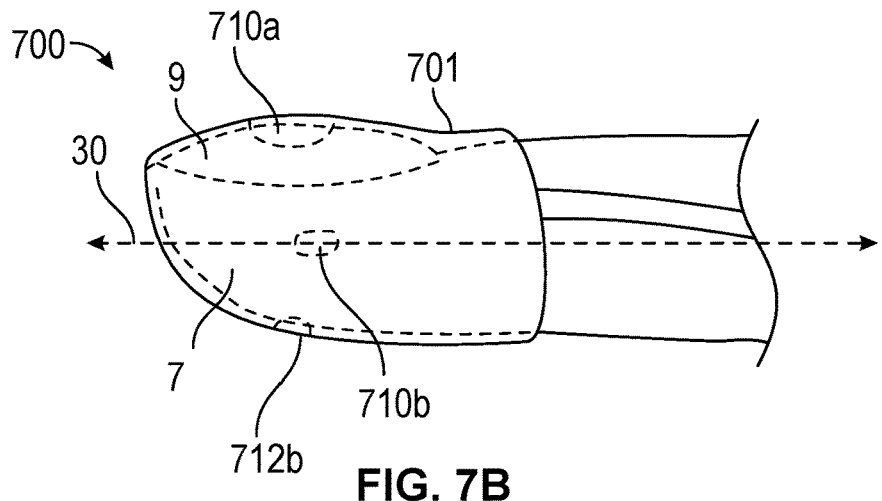
Figure 7C:
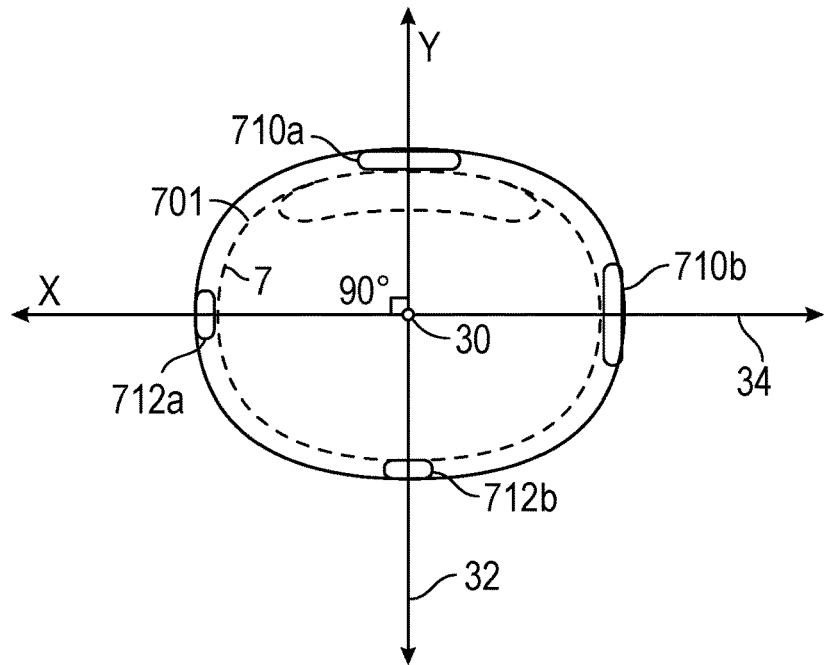
FIG. 7C illustrates a cross-sectional view of a portion of the sensor of FIGS. 7A-7B in accordance with aspects of this disclosure.

FIGS. 7A-7B illustrate side views of an example multi-emitter arrangement of a sensor 700 and FIG. 7C illustrates a cross-sectional view of the arrangement of FIGS. 7A-7B. As shown, the sensor 700 can include emitters 710a, 710b that are distributed in an area proximate the tissue site and detectors 712a, 712b that are distributed in an area proximate the tissue site. The emitters 710a, 710b and detectors 712a, 712b are shown in dotted lines in FIGS. 7A-7B and are shown in solid lines in FIG. 7C. The representation of the emitters 710a, 710b and the detectors 712a, 712b in solid or dotted lines is not meant to be limiting but is meant for illustrative purposes. Furthermore, the representation of the locations of the emitters 710a, 710b and/or detectors 712a, 712b in FIGS. 7A-7C is not meant to limiting of the location of the emitters 710a, 710b and/or detectors 712a, 712b. The emitters 710a, 710b and/or detectors 712a, 712b can be positioned on interior portions, exterior portions, and/or within (for example, within a thickness of) the sensor (for example, of a body portion of the sensor).

Sensor 700 can include a body portion 701 that can secure to and/or around a tissue site and can include and/or operably position the emitters 710a, 710b and detectors 712a, 712b. Body portion 701 can be similar or identical to any of body portions 201, 301, 401, or 501 discussed above. Sensor 700 can include and/or be configured to connect to a cable that can be similar or identical to cables 203, 303 of sensors 200, 300.

The spacing between and/or the arrangement of the detectors 712a, 712b, emitter 710a, and/or emitter 710b can vary across embodiments. For example, the emitters 710a, 710b and/or detectors 712a, 712b can be positioned or spaced to maximize a difference between the tissues sampled by each of the detectors 712a, 712b when the sensor 700 is in use. In some cases, the emitters 710a, 710b and detectors 712a, 712b can be equally circumferentially spaced at least partially around the tissue site when the sensor 600 is in use. Alternatively, in some cases, the emitters 710a, 710b and detectors 712a, 712b can be unequally circumferentially spaced about the tissue site when the sensor 600 is in use. For example, the arrangement or spatial distribution of the emitters 710a, 710b and detectors 712a, 712b can be random or arbitrary.

The relative position or arrangement of the emitters 710a, 710b and detectors 712a, 712b can be described with respect to a longitudinal axis 30 of the tissue site (e.g., angular displacement with respect to rotation about a longitudinal axis 30). For instance, with reference to FIGS. 7A-7B, the body portion 701 can operably position a first emitter 710a at a top side of the fingertip 7 (for example, at the nail-bed 9) and a second emitter 710b at a right or left side of the fingertip 7 circumferentially offset approximately 90 degrees from the first emitter 710a with respect to the longitudinal axis 30. Further, the body portion 701 can operably position a first detector 712b at a bottom side of the fingertip 7, opposite the first emitter 710a relative to the fingertip 7, and a second detector 712a at a right or left side of the fingertip 7, opposite the second emitter 710b relative to the fingertip 7 and circumferentially offset approximately 90 degrees from the first emitter 710a and the first detector 712b with respect to the longitudinal axis 30. The emitters 710a, 710b and detectors 712a, 712b can be aligned or otherwise located on a common plane defined by and/or defining a cross-section of the body portion 701. Alternatively, the emitters 710a, 710b and detectors 712a, 712b may not be aligned and/or not located on such a common plane defined by and/or defining a cross-section of the body portion 701.

Although the emitters 710a, 710b and detectors 712a, 712b are illustrated as being circumferentially spaced approximately 90 degrees from each other relative to the longitudinal axis 30 in FIG. 7C, this should not be construed as limiting. In some cases, the spacing can vary based on the total number of emitters and detectors. For example, given n number of emitters and detectors in sensor 700, each emitter and detector can be spaced circumferentially from another emitter or detector by 360/n degrees.

To facilitate variations in path lengths associated with transmitted and/or reflected light in tissue of the subject detected by detectors 712a, 712b, emitters 710a, 710b can be modulated and/or selectively activated so that only one of emitter 710a or emitter 710b is emitting light at a given time. In this way, the sensor 700 can generate several light paths and associated measurements, such as a first light path from emitter 710a to detector 712a, a second light path from emitter 710a to detector 712b, a third light path from emitter 710b to detector 712a, and/or a fourth light path from emitter 710b to detector 712b. In some implementations, emitter 710a can be activated for a first quarter cycle and off for the remaining three-quarters cycle and emitter 710b can be activated for a third quarter cycle and off for the remaining three-quarters cycle. In this way, the emitters 710a, 710b can be cycled on and off alternately, in sequence, with each only active for a quarter cycle and with a quarter cycle separating the active times. In some cases, additional measurements can be generated by activating both of emitters 710a, 710b for a period of time. Alternative activation sequences for the emitters 710a, 710b may be used in some cases, which can provide a time multiplexed signal from the detector 712a and/or 712b allowing separation of emitter signals.

The detectors 712a, 712b can generate one or more electrical signals corresponding to detected light after attenuation through tissue. In cases where emitters 710a, 710b are each activated for a period of time, the detectors 712a, 712b can be utilized to form a time-division-multiplexed (TDM) signal. This TDM signal can be coupled to a monitoring device. In some implementations, emitter 710a is configured to emit red light and emitter 710b is configured to emit infrared light, and the sensor 700 can be configured to facilitate obtaining a time multiplexed signal from the detectors 712a, 712b allowing separation of red and infrared signals and determination and removal of ambient light levels in downstream signal processing.

Sensor 700 can include a body portion 701 that can be similar or identical to body portion 201, 301, 401, 501 of sensor 200, 300, 400, 500, respectively. In some implementations, body portion 701 is a sleeve that can slide and/or be otherwise positioned over a portion of the subject's body (e.g., a finger). In some implementations, body portion 701 is configured to be wrapped around a portion of the subject's body. For example, in some implementations, sensor 700 is a tape sensor (such as shown in FIG. 6). As another example, in some implementations, portions of the body portion 701 are configured to wrap around a subject's finger and secure to other portions of the body portion 701.

Figure 7D:
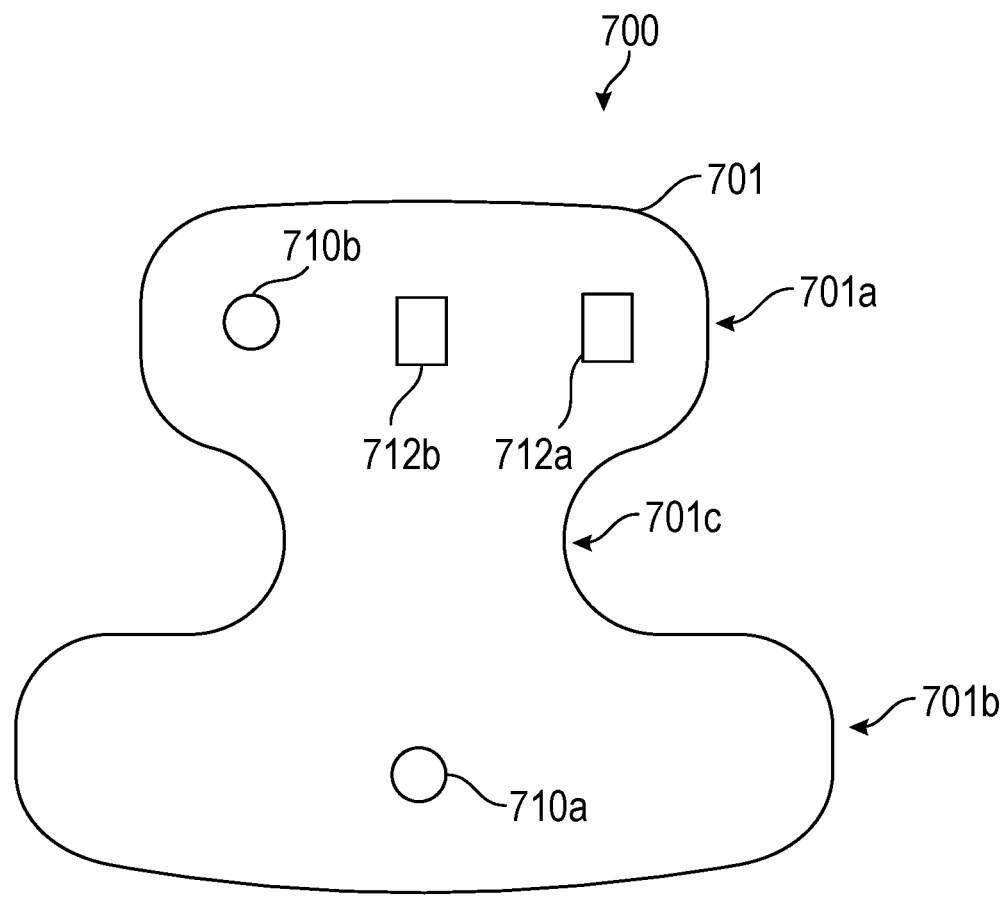
FIG. 7D illustrates the sensor of FIGS. 7A-7C in a first configuration in accordance with aspects of this disclosure.

FIG. 7D shows an illustrative implementation of body portion 701 of sensor 700. Body portion 701 can include a first portion 701*a*, a second portion 701*b*, and a third or intermediate portion 701*c* that can connect and be positioned between the first and second portions 701*a*, 701*b*. In some implementations, the intermediate portion 701*c* is smaller (for example, narrower) than one or both of portions 701*a*, 701*b*. FIG. 7D illustrates sensor 700 and body portion 701 in a first configuration where the body portion 701 is substantially flat and not secured to a subject's finger. FIG. 7D illustrates locations of the emitters 710*a*, 710*b* and detectors 712*a*, 712*b* in such first configuration. In such first configuration, the emitter 710*a* and detector 712*b* can be aligned with one another along a common axis. Additionally, in such first configuration, the emitter 710*b*, detector 712*a*, and detector 712*b* can be aligned with one another along a common axis.

To secure the sensor 700 to a subject's finger, the finger can be positioned over the first portion 701*a*, the second portion 701*b* can be wrapped around a tip of the finger, and portions of the first and second portions 701*a*, 701*b* can be secured to one another, for example, via adhesive securement and/or mechanical securement (for example, via hook and loop fastener type engagement). In such manner, body portion 701 can be transitioned from a first configuration where it is flat and/or not secured to the finger (see FIG. 7D) to a second configuration where it is secured to the finger (see FIG. 7A-7C). In some implementations, when body portion 701 is in such second configuration, a cross-section of body portion 701 is rounded (see FIG. 7C).

It is to be understood that sensor 700 can be secured to a finger in a variety of ways. For example, body portion 701 can be secured to a finger such that the emitter 710*a* and detector 712*b* are positioned at a top side or a bottom side of the finger and detector 712*a* and emitter 710*b* are positioned at right or left sides of the finger. In some cases, the sensor 700 (for example, body portion 701) can be sized and/or shaped such that, when positioned over a fingertip, sensor 700 (for example, body portion 701) does not cover the subject's knuckles.

Movable Emitter or Detector Arrangement

In some cases, an emitter or detector of a sensor, or the sensor itself, can be enabled for manual or automated movement to alternate positions, for example relative to a tissue site of a subject and/or relative to various components of the sensor. Similar to the multi-detector or multi-emitter arrangements described herein, such a sensor can be configured to output multiple signals corresponding to varying path lengths. For example, the sensor can be utilized for a first measurement at a first location and can be utilized for a second measurement at a second location.

Figure 8:
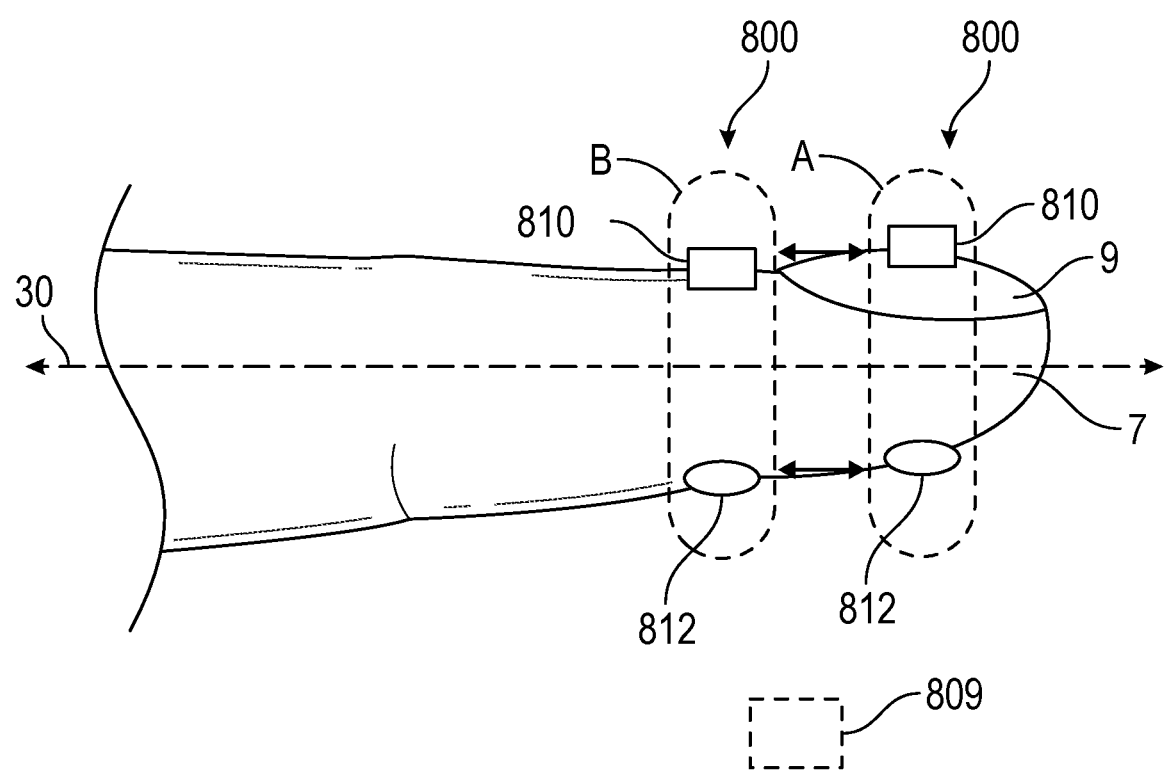
FIG. 8 depicts an example transitional sequence of a sensor moving between alternate positions in accordance with aspects of this disclosure.

FIG. 8 depicts an example transitional sequence as a sensor 800 moves between alternate positions, A and B, along a subject's finger 7. The sensor 800 can include one or more emitters and one or more detectors. For example, sensor 800 can include an emitter 810 and a detector 812. At position A, the sensor 800 is closer to a distal end of the finger, and at position B, the sensor 800 is further from the distal end of the finger. Although the illustrated sensor includes a single emitter 810 and a single detector 812, it will be understood that the sensor of FIG. 8 can include an alternative number of emitters, detectors, or configurations (for example, multi-detector arrangement, multi-emitter arrangement).

In some cases, the entire sensor 800 is configured to be moveable. In some cases, only a portion of the sensor 800 is configured to be moveable. For example, in some cases, an emitter 810 is movable, while a detector 812 is not. As another example, a detector 812 can be movable while an emitter 810 is not.

The sensor 800, or portions thereof, can be manually moved, for example by a user. In some such cases, the sensor 800 can include a position changer 809, such as a wheel, knob, button, switch, slider, rail, etc. For example, a user could place the sensor 800 at a first position (for example, position A) and then move it to a second position (for example, position B) by interacting with the position changer 809. In some cases, a display or other indication can prompt the user to cause the sensor 800 to move to the second position and/or can display readings after measurements are complete.

Additionally or alternatively, the sensor 800, or portions thereof, may be configured to be moved by an automated or motorized arrangement. For example, a position changer 809 can be configured to interact with and move the sensor 800, automatically, as desired or required. The position changer 809 can vary across embodiments. For example, the position changer 809 can include, but is not limited to, a motor, actuator, micro-motor, or solenoid actuator arrangement. In some such cases, motion control can be software programmed. The number of positions of sensor 800 can vary across embodiments and can be fixed or variable. For example, in some cases, the sensor 800 can be configured to move within a limited range of motion between alternate positions. Similar to any of the other sensors described herein, the sensor 800 can output signals corresponding to varying path lengths. For example, the sensor 800 may be configured to obtain a measurement at each of a plurality of positions of the sensor 800, thereby obtaining measurements at different tissue geometries. In some implementations, sensor 800 includes a body portion and/or cable, each of which can be similar or identical to any of the body portions and/or cables discussed elsewhere herein.

Sensor With Dual Transmittance and Reflectance Functionality

Figure 9A:
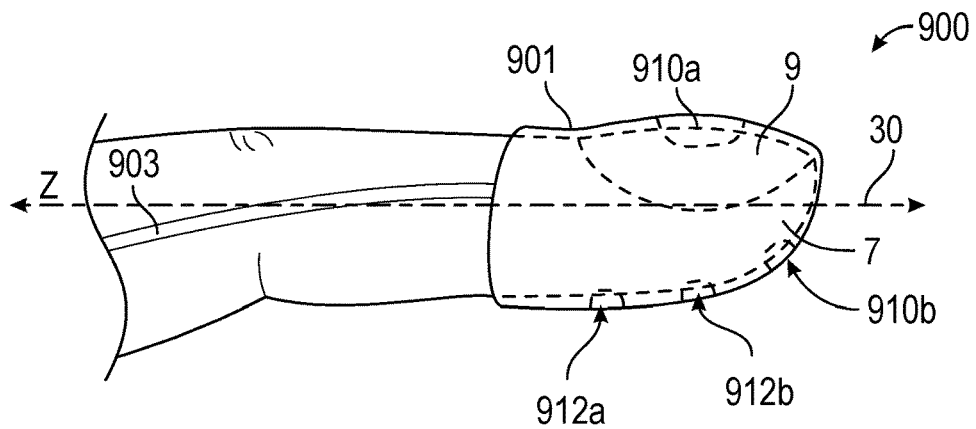
FIG. 9A illustrates another embodiment of a sensor in accordance with aspects of this disclosure.
Figure 9B:
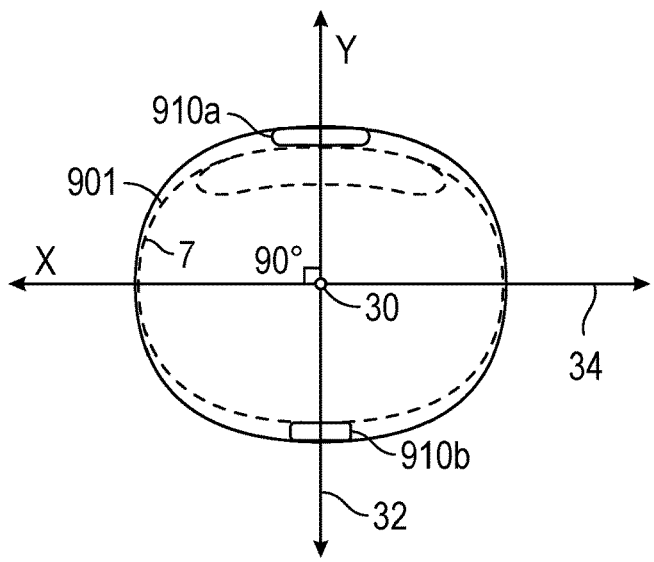
FIGS. 9B-9C illustrate cross-sectional views of portions of the sensor of FIG. 9A in accordance with aspects of this disclosure.
Figure 9C:
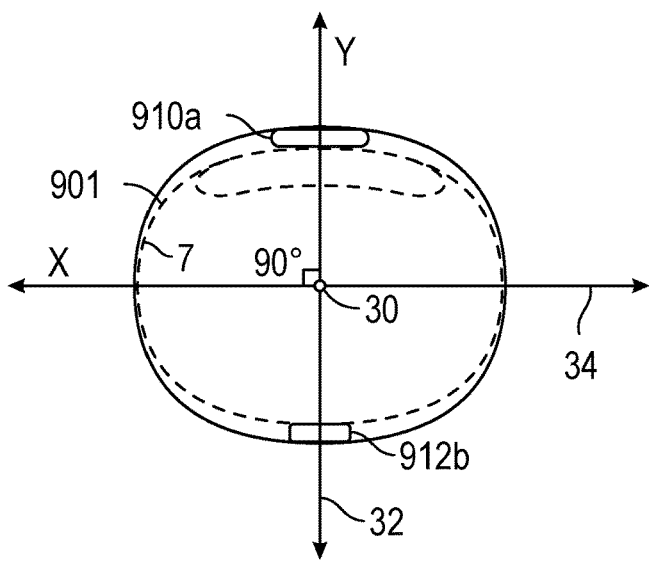

FIGS. 9A-9F illustrate a sensor 900. As discussed further below, sensor 900 can include multiple emitters and/or multiple detectors that can be utilized to allow the sensor 900 to operate in either or both of transmittance and reflectance pulse oximetry modes. FIGS. 9B-9C illustrate cross-sectional representational views of the arrangement of FIG. 9A. The sensor 900 can be configured to be worn and/or to secure to a tissue site on a user. For example, the sensor 900 can be configured to secure to a finger of a user. With reference to FIG. 9A, the sensor 900 can comprise a body portion 901 configured to secure and/or operably position detectors 912*a*, 912*b* and emitters 910*a*, 910*b*. The body portion 901 can be similar or identical to any of body portions 201, 301, 401, 501, 701 of sensors 200, 300, 400, 500, 700. In some implementations, body portion 901 is a sleeve that can slide and/or be otherwise positioned over a portion of the subject's body (e.g., a finger). In some implementations, body portion 901 is configured to be wrapped around a portion of the subject's body. For example, in some implementations, sensor 900 is a tape sensor (such as shown in FIG. 6). As another example, in some implementations, portions of the body portion 901 are configured to wrap around a subject's finger and secure to other portions of the body portion 901. In some implementations, sensor 900 includes a cable 903. Cable 903 can be similar or identical to cables 203, 303 discussed above.

Figure 9D:
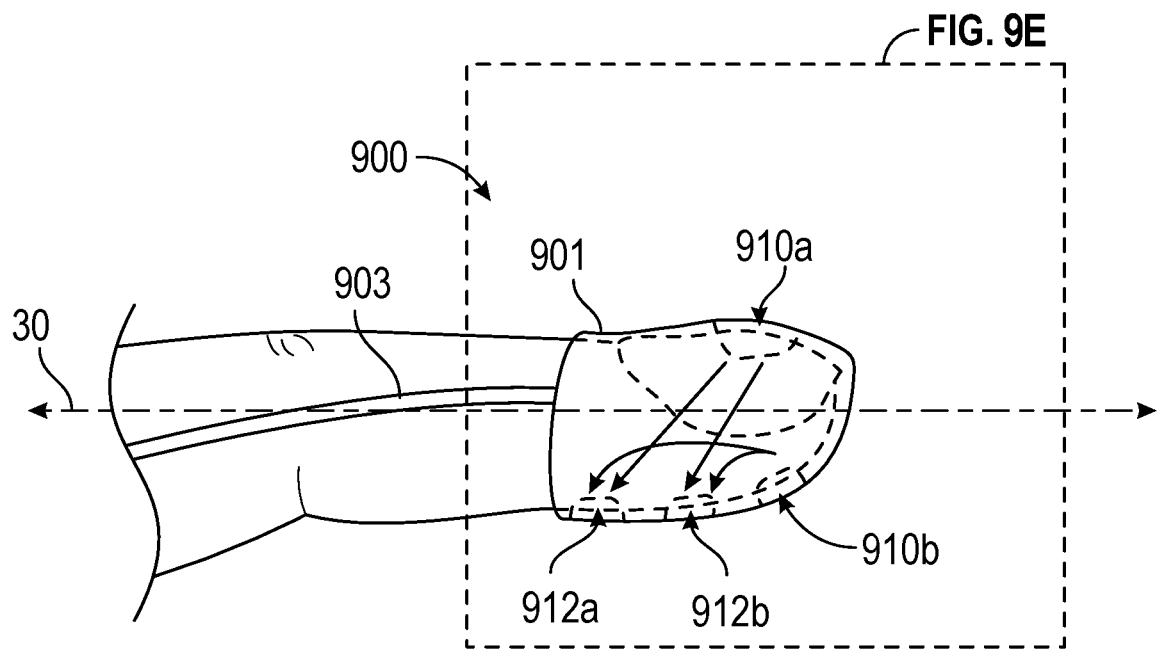
FIGS. 9D-9E schematically illustrate example light transmittance and reflectance for the sensor of FIG. 9A in accordance with aspects of this disclosure.
Figure 9E:
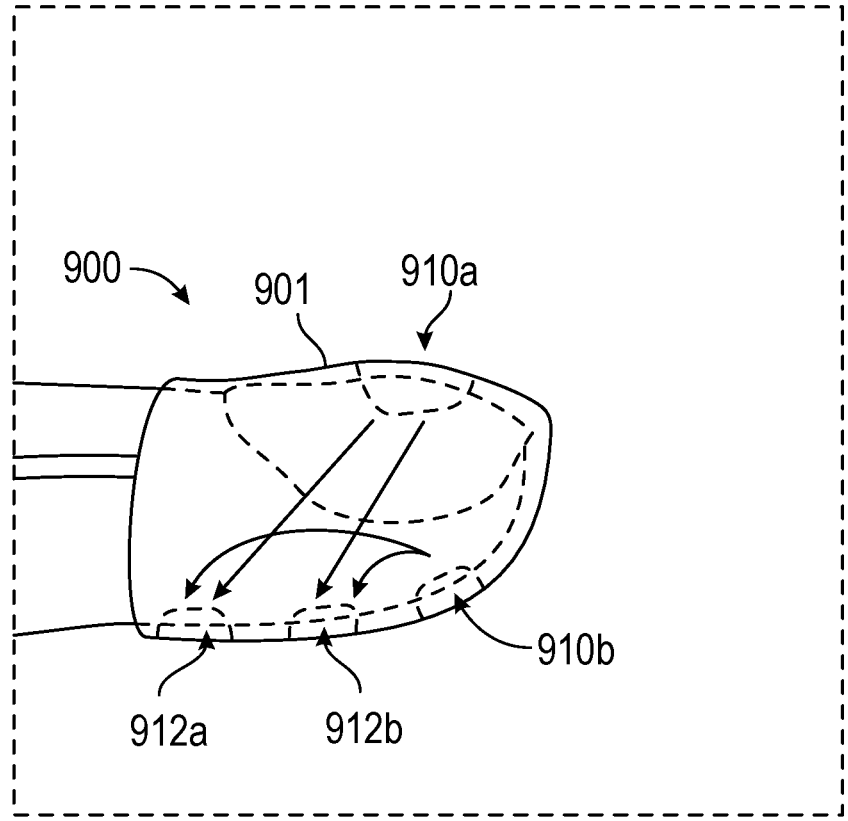

The emitters 910a, 910b and detectors 912a, 912b are shown in dotted lines in FIGS. 9A, 9D, and 9E and are shown in solid lines in FIGS. 9B-9C. The representation of the emitters 910a, 910b and the detectors 912a, 912b in solid or dotted lines is not meant to be limiting but is meant for illustrative purposes. Furthermore, the representation of the locations of the emitters 910a, 910b and/or detectors 912a, 912b in FIGS. 9A-9E is not meant to limiting of the location of the emitters 910a, 910b and/or detectors 912a, 912b. The emitters 910a, 910b and/or detectors 912a, 912b can be positioned on interior portions, exterior portions, and/or within (for example, within a thickness of) the sensor (for example, of a body portion of the sensor).

Figure 9F:
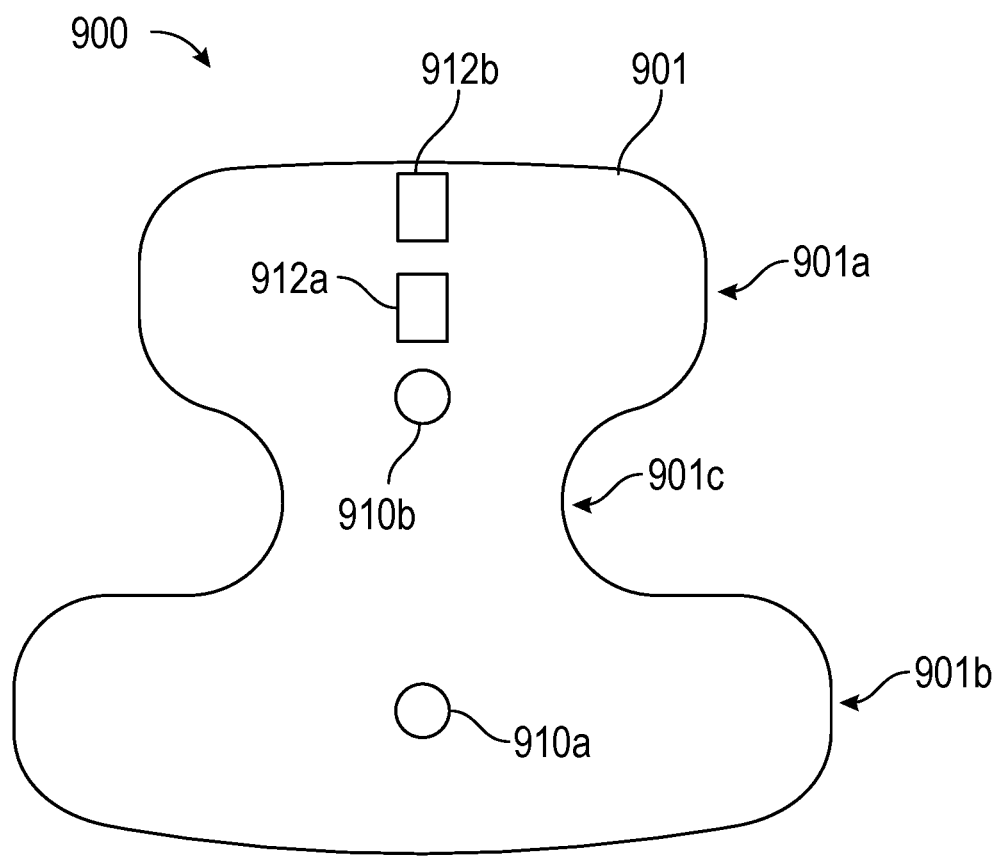
FIG. 9F illustrates the sensor of FIGS. 9A-9E in a first configuration in accordance with aspects of this disclosure.

FIG. 9F shows an illustrative implementation of body portion 901. Body portion 901 can include a first portion 901a, a second portion 901b, and a third or intermediate portion 901c that can connect and be positioned between the first and second portions 901a, 901b. In some implementations, the intermediate portion 901c is smaller (for example, narrower) than one or both of portions 901a, 901b. FIG. 9F illustrates sensor 900 and body portion 901 in a first configuration where the body portion 901 is substantially flat and not secured to a subject's finger. FIG. 9F illustrates locations of the emitter 910a, emitter 910b, and detectors 912a, 912b in such first configuration. In such first configuration, the emitters 910a, 910b and detectors 912a, 912b can all be aligned with one another along a common axis.

To secure the sensor 900 to a subject's finger, the finger can be positioned over the first portion 901a, the second portion 901b can be wrapped around a tip of the finger, and portions of the first and second portions 901a, 901b can be secured to one another, for example, via adhesive securement and/or mechanical securement (for example, via hook and loop fastener type engagement). In such manner, body portion 901 can be transitioned from a first configuration where it is flat and/or not secured to the finger (see FIG. 9F) to a second configuration where it is secured to the finger (see FIGS. 9A-9E). In some implementations, when body portion 901 is in such second configuration, a cross-section of body portion 901 is rounded (see FIGS. 9B-9C).

It is to be understood that sensor 900 can be secured to a finger in a variety of ways. For example, body portion 901 can be secured to a finger such that the emitter 910a is positioned at a top side or a bottom side of the finger and emitter 910b and detectors 912a, 912b are positioned at a top side or a bottom side of the finger. In some cases, the sensor 900 (for example, body portion 901) can be sized and/or shaped such that, when positioned over a fingertip, sensor 900 (for example, body portion 901) does not cover the subject's knuckles.

In some implementations, as illustrated in FIGS. 9A-9C, the emitter 910a may be aligned with one or more of the detectors 912a, 912b and the emitter 910b along a common axis. For example, the emitter 910a may be aligned with the emitter 910b, and detectors 912a, 912b such that they are all positioned on a plane extending along the Y axis 32 and Z axis 30 (see FIGS. 9A-9C). However, in alternative implementations, one or more of the detectors 912a, 912b and the emitter 910b may not be positioned on such a plane, for example, one or more of the detectors 912a, 912b and the emitter 910b can be positioned at various locations at the bottom, left, or right sides of the finger when body portion 901 is secured to the finger.

FIGS. 9D-9E illustrate how sensor 900 can operate in either or both of transmittance and reflectance pulse oximetry modes. Arrows appearing in FIGS. 9D-9E illustrate exemplary paths of light traveling through portions of the finger during such modes. For example, the arrows extending from emitter 910a to each of detectors 912a. 912b illustrate exemplary paths of light in a transmittance mode. Additionally, the arrows from emitter 910b to each of detectors 912a, 912b illustrate exemplary paths of light in a reflectance mode. Each of detectors 912a, 912b can generate one or more electrical signals responsive to receiving such transmitted and/or reflected light that has attenuated through tissue of the finger. Sensor 900 can be configured to operate in such transmittance and reflectance modes concurrently or non-concurrently. In some implementations, emitters 910a, 910b can be each activated for a period of time and the detectors 912a, 912b can be utilized to form a time-division-multiplexed (TDM) signal. This TDM signal can be coupled to a monitoring device. In some implementations, emitter 910a can be activated for a first quarter cycle and off for the remaining three-quarters cycle and emitter 910b can be activated for a third quarter cycle and off for the remaining three-quarters cycle. In this way, the emitters 910a, 910b can be cycled on and off alternately, in sequence, with each only active for a quarter cycle and with a quarter cycle separating the active times. In some cases, additional measurements can be generated by activating both of emitters 910a, 910b for a period of time. Alternative activation sequences for the emitters 910a, 910b may be used in some cases, which can provide a time multiplexed signal from the detector 912a and/or 912b allowing separation of emitter signals. In some implementations, emitter 910a is configured to emit red light and emitter 910b is configured to emit infrared light, and the sensor 900 can be configured to facilitate obtaining a time multiplexed signal from the detectors 912a, 912b allowing separation of red and infrared signals and determination and removal of ambient light levels in downstream signal processing.

In some implementations, the emitters 910a, 910b may emit light in an alternating fashion such that the detectors 912a, 912b can detect the transmitted light and the reflected light. For example, when the emitter 910a emits light, the detectors 912a, 912b can detect light transmitted from the emitter 910a to the detectors 912a, 912b through tissue of the finger. When the emitter 910b emits light (for example, while the emitter 910a is turned off), the detectors 912a, 912b can detect light emitted by the emitter 910b and reflected by the tissue. In some implementations, one or more signals generated by the detectors 912a, 912b during a transmittance mode (for example, where only emitter 910a is active) are analyzed separately from one or more signals generated by the detectors 912a, 912b during a reflectance mode (for example, where only emitter 910b is active). In some implementations, for example, where the sensor 900 is configured to operate in transmittance and reflectance modes concurrently, signals generated by the detectors 912a, 912b that are based on light emitted from both of emitters 910a, 910b are analyzed together and/or are compared.

Utilizing both transmittance and reflectance pulse oximetry modes during operation (whether concurrently or non-concurrently) via multiple detectors and/or multiple emitters can advantageously allow the sensor 900 to generate signals that correspond to different path lengths and/or different tissue geometries. In some implementations, physiological measurements (for example, blood oxygen saturation) of a patient can be obtained using, for example, transmittance and reflectance operational modes. Accordingly, using both transmittance and reflectance can improve the accuracy, reliability, and/or robustness of a physiological sensor by reducing the likelihood of a measurement error (for example, compared to measurements made using just transmittance or just reflectance). Additionally, use of reflectance can increase the number of areas where a sensor may be placed on a subject.

Any of the sensors or portions thereof described herein can be integrated into an apparatus that can be worn by a subject. Such apparatus, which can be wearable by the subject, can be a sleeve (for example, fingertip sleeve, arm sleeve, wrist sleeve, leg sleeve, toe sleeve, and the like), a finger clip, an ear clip, an ear insert, a toe clip, a glove, a ring, a bracelet, a watch, an arm band, a sock, an ankle band, a wrap, or another apparatus that can be worn or attached to a subject.

Any of the sensors 200, 300, 400, 500, 600, 700, 800, and/or 900 can be configured to interact with a separate device (such as monitoring device 80) in a similar or identical manner as that described above with respect to sensor 100. Additionally, any of sensors 200, 300, 400, 500, 600, 700, 800, and/or 900 can include features of monitoring device 80 similar to that described with reference to sensor 100. For example, any of sensors 200, 300, 400, 500, 600, 700, 800, and/or 900 can be configured to determine one or more physiological parameters (for example, via a processor thereof) and/or to communicate (for example, wirelessly) with separate devices.

In various ones of the figures, emitter(s) and/or detector(s) may be represented by various shapes having various sizes. Such shapes and/or sizes are not intended to be limiting, however, and the relative sizes and/or shapes of any of the emitters and/or detectors shown in the figures are not intended to be limiting.

TERMINOLOGY

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figures. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A noninvasive physiological sensor configured to attach to a finger of a user, the noninvasive physiological sensor comprising:
    a body portion configured to be secured to a finger of a user, the body portion comprising:
        a first portion;
        a second portion positioned axially from the first portion, the second portion wider than the first portion; and
        an intermediate portion positioned between the first portion and the second portion and connected between the first portion and the second portion, the intermediate portion narrower than the first portion and the second portion;
    a first emitter configured to emit light of one or more wavelengths into tissue of the finger of the user when the noninvasive physiological sensor is in use, wherein the first emitter is configured to be operably positioned by the body portion at a first side of the finger when the body portion is configured to be secured to the finger, the first emitter arranged on the second portion; and
    a plurality of detectors, each of the plurality of detectors configured to detect at least a portion of the emitted light after attenuation by the tissue of the finger of the user when the noninvasive physiological sensor is in use, wherein each of the plurality of detectors is configured to generate at least one signal responsive to the detected light, and wherein the plurality of detectors comprises:
        a first detector configured to be operably positioned by the body portion at a second side of the finger that is opposite the first side of the finger when the body portion is configured to be secured to the finger such that the first detector and the first emitter are substantially aligned with one another; and
        a second detector configured to be operably positioned by the body portion at a third side of the finger when the body portion is configured to be secured to the finger such that the second detector is offset approximately 90 degrees from the first emitter with respect to an axis extending through at least a portion of the body portion, the first detector and the second detector arranged in an array on the first portion.

2. The noninvasive physiological sensor of claim 1, wherein:
    the noninvasive physiological sensor further comprises a second emitter configured to emit light of one or more wavelengths into the tissue of the finger of the user when the noninvasive physiological sensor is in use; and
    the second emitter is operably positioned by the body portion at a fourth side of the finger that is opposite the third side of the finger when the body portion is secured to the finger such that the second emitter is offset approximately 90 degrees from the first emitter with respect to said axis extending through at least the portion of the body portion.

3. The noninvasive physiological sensor of claim 2, wherein the second emitter is operably positioned by the body portion such that the second emitter is offset approximately 180 degrees from the second detector with respect to said axis extending through at least the portion of the body portion.

4. The noninvasive physiological sensor of claim 2, wherein the first emitter and the second emitter are configured to be selectively activated such that only one of the first and second emitters is emitting light at a given time.

5. The noninvasive physiological sensor of claim 1, wherein said axis extends through a center of a cross-section of the body portion.

6. The noninvasive physiological sensor of claim 1, wherein the first emitter and the plurality of detectors are operably positioned by the body portion along a plane of a cross-section of the body portion when secured to the finger of the user.

7. The noninvasive physiological sensor of claim 1, wherein said body portion is configured such that, when secured to the finger of the user, said axis extends along at least a portion of a longitudinal axis of the finger.

8. The noninvasive physiological sensor of claim 1, wherein said first emitter is the only emitter of the noninvasive physiological sensor.

9. The noninvasive physiological sensor of claim 1, wherein the body portion is configured to be transitioned from a first configuration when not secured to the finger of the user to a second configuration when secured to the finger of the user, and wherein the first and second configurations are different.

10. The noninvasive physiological sensor of claim 9, wherein the body portion is configured to be substantially flat when in the first configuration.

11. The noninvasive physiological sensor of claim 9, wherein the body portion is configured such that, when in the second configuration, the body portion is wrapped around the finger of the user.

12. The noninvasive physiological sensor of claim 9, wherein, when the body portion is in said second configuration, a cross-section of the body portion is rounded.

13. The noninvasive physiological sensor of claim 1, wherein the plurality of detectors further comprises a third detector operably positioned by the body portion at a fourth side of the finger when the body portion is secured to the finger such that the third detector is offset approximately 90 degrees from the first emitter with respect to said axis extending through said at least the portion of the body portion.

14. The noninvasive physiological sensor of claim 13, wherein the third detector is operably positioned by the body portion at the fourth side of the finger when the body portion is secured to the finger such that the third detector is offset approximately 180 degrees from the second detector with respect to said axis extending through at least the portion of the body portion.

15. The noninvasive physiological sensor of claim 1, wherein the first emitter and the plurality of detectors are in communication with a monitoring device configured to:
   control operation of the first emitter;
   receive said at least one signal generated by each of the plurality of detectors; and
   determine one or more physiological parameters based on said at least one signal generated by each of the plurality of detectors.

16. The noninvasive physiological sensor of claim 15, wherein the one or more physiological parameters comprises at least one of oxygen saturation, pulse rate, and glucose.

17. The noninvasive physiological sensor of claim 15, further comprising a cable connected to the body portion and configured to transmit said at least one signal generated by each of the plurality of detectors to said monitoring device.

18. The noninvasive physiological sensor of claim 15, wherein said monitoring device is configured to attach to a wrist of the user.

19. The noninvasive physiological sensor of claim 15, wherein said monitoring device is configured to wirelessly transmit said determined one or more physiological parameters.

20. The noninvasive physiological sensor of claim 15, wherein said noninvasive physiological sensor is configured to wirelessly transmit said at least one signal from each of the plurality of detectors to said monitoring device.

* * * * *